United States Patent
Esnouf

(10) Patent No.: US 10,576,230 B2
(45) Date of Patent: *Mar. 3, 2020

(54) ARTIFICIAL AIRWAY

(71) Applicant: TELEFLEX LIFE SCIENCES UNLIMITED COMPANY, Athlone, Co Westmeath (IE)

(72) Inventor: Philip Stuart Esnouf, Richmond (AU)

(73) Assignee: TELEFLEX LIFE SCIENCES UNLIMITED COMPANY, Athlone, Co Westmeath (IE)

( * ) Notice: Subject to any disclaimer, the term of this patent is extended or adjusted under 35 U.S.C. 154(b) by 1125 days.

This patent is subject to a terminal disclaimer.

(21) Appl. No.: 14/883,676

(22) Filed: Oct. 15, 2015

(65) Prior Publication Data

US 2016/0184542 A1    Jun. 30, 2016

Related U.S. Application Data

(63) Continuation of application No. 13/382,733, filed as application No. PCT/AU2010/000861 on Jul. 6, 2010, now Pat. No. 9,265,904.

(30) Foreign Application Priority Data

Jul. 6, 2009 (AU) ................................ 2009903153

(51) Int. Cl.
*A61M 16/00* (2006.01)
*A61M 16/04* (2006.01)

(52) U.S. Cl.
CPC ........ *A61M 16/0445* (2014.02); *A61M 16/04* (2013.01); *A61M 16/0409* (2014.02);
(Continued)

(58) Field of Classification Search
CPC .............. A61M 16/04; A61M 16/0488; A61M 16/0434; A61M 16/0816; A61M 16/0465;
(Continued)

(56) References Cited

U.S. PATENT DOCUMENTS 2,096,831 A    10/1937  Wappler
2,099,127 A    11/1937  Leech
(Continued)

FOREIGN PATENT DOCUMENTS

CA    2 012 750    9/1990
CA    2 067 782    5/1991
(Continued)

OTHER PUBLICATIONS

International Search Report of PCT/AU2010/000861, dated Sep. 29, 2010.
(Continued)

*Primary Examiner* — Steven O Douglas
(74) *Attorney, Agent, or Firm* — Sughrue Mion, PLLC

(57) ABSTRACT

An artificial airway including: an airway tube including at least one airway conduit; an inflatable cuff mounted on a distal end of the tube; a support member extending into the cuff, the cuff having inner side walls, anterior walls and a posterior wall, the inner side walls being joined to the support member to define a recess which communicates with the airway conduit, the anterior walls and posterior wall, sealingly engaging, in use, about the glottic opening and posterior pharyngeal wall respectively of a patient.

18 Claims, 22 Drawing Sheets

(52) U.S. Cl.
CPC .... *A61M 16/0415* (2014.02); *A61M 16/0443* (2014.02); *A61M 16/0463* (2013.01); *A61M 16/0434* (2013.01); *A61M 16/0493* (2014.02)

(58) Field of Classification Search
CPC .......... A61M 16/0463; A61M 16/0409; A61M 16/0415; A61M 16/0445
See application file for complete search history.

(56) References Cited

U.S. PATENT DOCUMENTS

| | | |
|---|---|---|
| 2,252,874 A | 8/1941 | Vischer et al. |
| 2,839,788 A | 6/1958 | Dembiak |
| 2,862,498 A | 12/1958 | Weeles |
| 3,124,959 A | 3/1964 | Pall et al. |
| 3,529,596 A | 9/1970 | Garner |
| 3,554,673 A | 1/1971 | Schwartz et al. |
| 3,683,908 A | 8/1972 | Michael et al. |
| 3,794,036 A | 2/1974 | Carroll |
| 3,931,822 A | 1/1976 | Marici |
| 4,056,104 A | 11/1977 | Jaffe |
| 4,067,329 A | 1/1978 | Winicki et al. |
| 4,096,759 A | 6/1978 | Desor |
| 4,104,357 A | 8/1978 | Blair |
| 4,116,201 A | 9/1978 | Shah |
| 4,134,407 A | 1/1979 | Elam |
| 4,159,722 A | 7/1979 | Walker |
| 4,178,938 A | 12/1979 | Au et al. |
| 4,178,940 A | 12/1979 | Au et al. |
| 4,231,365 A | 11/1980 | Scarberry |
| 4,256,099 A | 3/1981 | Dryden |
| 4,285,340 A | 8/1981 | Gezari et al. |
| 4,351,330 A | 9/1982 | Scarberry |
| 4,445,366 A | 5/1984 | Gray |
| 4,446,864 A | 5/1984 | Watson et al. |
| 4,471,775 A | 9/1984 | Clair et al. |
| 4,501,273 A | 2/1985 | McGinnis |
| 4,509,514 A | 4/1985 | Brain et al. |
| 4,510,273 A | 4/1985 | Miura et al. |
| 4,526,196 A | 7/1985 | Pistillo |
| 4,553,540 A | 11/1985 | Straith |
| 4,583,917 A | 4/1986 | Shah |
| 4,630,606 A | 12/1986 | Weerda et al. |
| 4,689,041 A | 8/1987 | Corday et al. |
| 4,700,700 A | 10/1987 | Eliachar |
| 4,770,170 A | 9/1988 | Sato et al. |
| 4,793,327 A | 12/1988 | Frankel |
| 4,798,597 A | 1/1989 | Vaillancourt |
| 4,825,862 A | 5/1989 | Sato et al. |
| 4,832,020 A | 5/1989 | Augustine |
| 4,850,349 A | 7/1989 | Farahany |
| 4,856,510 A | 8/1989 | Kowalewski et al. |
| 4,872,483 A | 10/1989 | Shah |
| 4,924,862 A | 5/1990 | Levinson |
| 4,953,547 A | 9/1990 | Poole, Jr. |
| 4,972,963 A | 11/1990 | Guarriello et al. |
| 4,981,470 A | 1/1991 | Bombeck, IV |
| 4,995,388 A | 2/1991 | Brain |
| 5,038,766 A | 8/1991 | Parker |
| 5,042,469 A | 8/1991 | Augustine |
| 5,042,476 A | 8/1991 | Smith |
| 5,060,647 A | 10/1991 | Alessi |
| 5,067,496 A | 12/1991 | Eisele |
| 5,113,875 A | 5/1992 | Bennett |
| 5,174,283 A | 12/1992 | Parker |
| 5,203,320 A | 4/1993 | Augustine |
| 5,218,970 A | 6/1993 | Turnbull et al. |
| 5,235,973 A | 8/1993 | Levinson |
| 5,237,988 A | 8/1993 | McNeese |
| 5,241,325 A | 8/1993 | Nguyen et al. |
| 5,241,656 A | 9/1993 | Brain |
| 5,241,956 A | 9/1993 | Brain et al. |
| 5,249,571 A | 10/1993 | Brain et al. |
| 5,273,537 A | 12/1993 | Haskvitz et al. |
| 5,277,178 A | 1/1994 | Dingley et al. |
| 5,282,464 A | 2/1994 | Brain et al. |
| 5,297,547 A | 3/1994 | Brain et al. |
| 5,303,697 A | 4/1994 | Brain et al. |
| 5,305,743 A | 4/1994 | Brain |
| 5,311,861 A | 5/1994 | Miller et al. |
| 5,331,967 A | 7/1994 | Akerson et al. |
| 5,339,805 A | 8/1994 | Parker |
| 5,339,808 A | 8/1994 | Don Michael |
| 5,355,879 A | 10/1994 | Brain et al. |
| 5,361,753 A | 11/1994 | Pothmann et al. |
| 5,391,248 A | 2/1995 | Brain et al. |
| 5,400,771 A | 3/1995 | Pirak et al. |
| 5,421,325 A | 6/1995 | Cinberg et al. |
| 5,438,982 A | 8/1995 | MacIntyre |
| 5,443,063 A | 8/1995 | Greenberg |
| 5,452,715 A | 9/1995 | Boussignac et al. |
| 5,459,700 A | 10/1995 | Jacobs |
| 5,487,383 A | 1/1996 | Levinson |
| 5,529,582 A | 6/1996 | Fukuhara et al. |
| 5,546,935 A | 8/1996 | Champeau |
| 5,546,936 A | 8/1996 | Virag et al. |
| 5,551,420 A | 9/1996 | Lurie et al. |
| 5,554,673 A | 9/1996 | Shah |
| 5,569,219 A | 10/1996 | Hakki et al. |
| 5,577,693 A | 11/1996 | Corn |
| 5,582,167 A | 12/1996 | Joseph |
| 5,584,290 A | 12/1996 | Brain et al. |
| 5,599,301 A | 2/1997 | Jacobs et al. |
| 5,623,921 A | 4/1997 | Kinsinger et al. |
| 5,626,151 A | 5/1997 | Linden |
| 5,632,271 A | 5/1997 | Brain et al. |
| RE35,531 E | 6/1997 | Callaghan et al. |
| 5,653,229 A | 8/1997 | Greenberg |
| 5,655,528 A | 8/1997 | Pagan et al. |
| 5,682,880 A | 11/1997 | Brain et al. |
| 5,692,498 A | 12/1997 | Lurie et al. |
| 5,694,929 A | 12/1997 | Christopher |
| 5,711,293 A | 1/1998 | Brain et al. |
| 5,738,094 A | 4/1998 | Hoftman |
| 5,743,254 A | 4/1998 | Parker |
| 5,743,258 A | 4/1998 | Sato et al. |
| 5,746,202 A | 5/1998 | Pagan et al. |
| 5,771,889 A | 6/1998 | Pagan et al. |
| 5,778,872 A | 7/1998 | Fukunaga et al. |
| 5,791,341 A | 8/1998 | Bullard |
| 5,794,617 A | 8/1998 | Brunell et al. |
| 5,816,240 A | 10/1998 | Komesaroff |
| 5,819,723 A | 10/1998 | Joseph |
| 5,832,916 A | 11/1998 | Lundberg et al. |
| 5,850,832 A | 12/1998 | Chu |
| 5,855,203 A | 1/1999 | Matter |
| 5,856,510 A | 1/1999 | Meng et al. |
| 5,860,418 A | 1/1999 | Lundberg et al. |
| 5,865,176 A | 2/1999 | O'Neil et al. |
| 5,878,745 A | 3/1999 | Brian |
| 5,881,726 A | 3/1999 | Neame |
| 5,893,891 A | 4/1999 | Zahedi et al. |
| 5,896,858 A | 4/1999 | Brain |
| 5,915,383 A | 6/1999 | Pagan |
| 5,921,239 A | 7/1999 | McCall et al. |
| 5,924,862 A | 7/1999 | White |
| 5,935,084 A | 8/1999 | Southworth |
| 5,937,860 A | 8/1999 | Cook |
| 5,957,133 A | 9/1999 | Hart |
| 5,976,075 A | 11/1999 | Beane et al. |
| 5,979,445 A | 11/1999 | Neame et al. |
| 5,983,891 A | 11/1999 | Fukunaga |
| 5,983,896 A | 11/1999 | Fukunaga et al. |
| 5,983,897 A | 11/1999 | Pagan |
| 5,988,167 A | 11/1999 | Kamen |
| 5,996,582 A | 12/1999 | Turnbull |
| 6,003,510 A | 12/1999 | Anunta |
| 6,003,511 A | 12/1999 | Fukunaga et al. |
| 6,003,514 A | 12/1999 | Pagan |
| 6,012,452 A | 1/2000 | Pagan |
| 6,021,779 A | 2/2000 | Pagan |
| 6,050,264 A | 4/2000 | Greenfield |
| 6,062,219 A | 5/2000 | lurie et al. |
| 6,070,581 A | 6/2000 | Augustine et al. |

(56) References Cited

U.S. PATENT DOCUMENTS

| | | |
|---|---|---|
| 6,079,409 A | 6/2000 | Brain et al. |
| D429,811 S | 8/2000 | Bermudez et al. |
| 6,095,144 A | 8/2000 | Pagan |
| 6,098,621 A | 8/2000 | Esnouf et al. |
| 6,110,143 A | 8/2000 | Kamen |
| 6,116,243 A | 9/2000 | Pagan |
| 6,119,695 A | 9/2000 | Augustine et al. |
| 6,131,571 A | 10/2000 | Lampotang et al. |
| 6,149,603 A | 11/2000 | Parker |
| 6,155,257 A | 12/2000 | Lurie et al. |
| 6,213,120 B1 | 4/2001 | Block et al. |
| 6,224,562 B1 | 5/2001 | Lurie et al. |
| 6,234,985 B1 | 5/2001 | Lurie et al. |
| 6,240,922 B1 | 6/2001 | Pagan |
| 6,251,093 B1 | 6/2001 | Valley et al. |
| 6,269,813 B1 | 8/2001 | Fitzgerald et al. |
| 6,315,739 B1 | 11/2001 | Merilainen et al. |
| 6,338,343 B1 | 1/2002 | Augustine et al. |
| 6,352,077 B1 | 3/2002 | Shah |
| 6,386,199 B1 | 5/2002 | Alfery |
| 6,390,093 B1 | 5/2002 | Mongeon |
| 6,422,239 B1 | 7/2002 | Cook |
| 6,427,686 B2 | 8/2002 | Augustine et al. |
| 6,439,232 B1 | 8/2002 | Brain |
| 6,450,164 B1 | 9/2002 | Banner et al. |
| 6,508,250 B1 | 1/2003 | Esnouf |
| 6,546,931 B2 | 4/2003 | Lin et al. |
| 6,631,720 B1 | 10/2003 | Braun et al. |
| 6,647,984 B1 | 11/2003 | O'Dea et al. |
| 6,651,666 B1 | 11/2003 | Owens |
| 6,705,318 B1 | 3/2004 | Brain |
| 6,766,801 B1 | 7/2004 | Wright |
| 7,004,169 B2 | 2/2006 | Brain et al. |
| 7,040,322 B2 | 5/2006 | Fortuna et al. |
| 7,051,096 B1 | 5/2006 | Krawiec et al. |
| 7,051,736 B2 | 5/2006 | Banner et al. |
| 7,096,868 B2 | 8/2006 | Tateo et al. |
| 7,097,802 B2 | 8/2006 | Brain et al. |
| 7,128,071 B2 | 10/2006 | Brain et al. |
| 7,134,431 B2 | 11/2006 | Brain et al. |
| 7,156,100 B1 | 1/2007 | Brain et al. |
| 7,159,589 B2 | 1/2007 | Brain |
| RE39,938 E | 12/2007 | Brain |
| 7,383,736 B2 | 6/2008 | Esnouf |
| 7,694,682 B2 | 4/2010 | Petersen et al. |
| 7,895,497 B2 | 2/2011 | Pisek et al. |
| 7,997,274 B2 | 8/2011 | Baska |
| 8,033,176 B2 | 10/2011 | Esnouf |
| 2002/0026178 A1 | 2/2002 | Ouchi |
| 2003/0000534 A1 | 2/2003 | Alfery |
| 2003/0037790 A1 | 2/2003 | Brian |
| 2003/0051734 A1 | 3/2003 | Brain |
| 2003/0101998 A1 | 6/2003 | Zocca et al. |
| 2003/0131845 A1 | 7/2003 | Lin |
| 2003/0172925 A1 | 9/2003 | Zocca et al. |
| 2003/0172935 A1 | 9/2003 | Miller |
| 2004/0020491 A1 | 2/2004 | Fortuna |
| 2004/0089307 A1 | 5/2004 | Brain |
| 2005/0066975 A1 | 3/2005 | Brain |
| 2005/0081861 A1 | 4/2005 | Nasir |
| 2005/0139220 A1 | 6/2005 | Christopher |
| 2005/0178388 A1 | 8/2005 | Kuo |
| 2005/0182295 A1 | 8/2005 | Soper et al. |
| 2005/0199244 A1 | 9/2005 | Tateo et al. |
| 2005/0274383 A1 | 12/2005 | Brain |
| 2006/0124132 A1 | 6/2006 | Brain |
| 2006/0180156 A1 | 8/2006 | Baska |
| 2006/0201516 A1 | 9/2006 | Petersen et al. |
| 2006/0254596 A1 | 11/2006 | Brain |
| 2007/0240722 A1 | 10/2007 | Kessler |
| 2008/0041392 A1 | 2/2008 | Cook |
| 2008/0099026 A1 | 5/2008 | Chang |
| 2008/0142017 A1 | 6/2008 | Brain |
| 2008/0276936 A1 | 11/2008 | Cook |
| 2008/0308109 A1 | 12/2008 | Brain |
| 2009/0133701 A1 | 5/2009 | Brain |
| 2009/0139524 A1 | 6/2009 | Esnouf |
| 2009/0145438 A1 | 6/2009 | Brain |
| 2010/0059061 A1 | 3/2010 | Brain |
| 2011/0023890 A1 | 2/2011 | Baska |
| 2011/0226256 A1 | 9/2011 | Dubach |
| 2011/0245805 A1 | 10/2011 | Swinehart et al. |
| 2012/0085351 A1 | 4/2012 | Brain |
| 2012/0145161 A1 | 6/2012 | Brain |
| 2012/0174929 A1 | 7/2012 | Esnouf |
| 2012/0186510 A1 | 7/2012 | Esnouf |
| 2014/0034060 A1 | 2/2014 | Esnouf et al. |

FOREIGN PATENT DOCUMENTS

| | | |
|---|---|---|
| CA | 2 141 167 A1 | 7/1995 |
| CN | 1166138 A | 11/1997 |
| CN | 1378470 A | 11/2002 |
| CN | 2579352 Y | 10/2003 |
| CN | 1688357 A | 10/2005 |
| CN | 1863568 A | 11/2006 |
| CN | 2882657 Y | 3/2007 |
| CN | 101057994 A | 10/2007 |
| CN | 101193677 A | 6/2008 |
| CN | 100531818 C | 8/2009 |
| CN | 201516220 U | 6/2010 |
| CN | 1213777 C | 8/2010 |
| CN | 201684261 U | 12/2010 |
| CN | 101991898 A | 3/2011 |
| CN | 103221087 B | 8/2016 |
| DE | 29 45 662 A1 | 5/1981 |
| DE | 4447186 A1 | 7/1996 |
| DE | 100 42 172 A1 | 4/2001 |
| EP | 0 294 200 A2 | 12/1988 |
| EP | 0 294 200 B1 | 12/1988 |
| EP | 0 389 272 A2 | 9/1990 |
| EP | 0 402 872 A1 | 12/1990 |
| EP | 0 580 385 A1 | 1/1994 |
| EP | 0 712 638 A1 | 5/1996 |
| EP | 0712638 A1 | 5/1996 |
| EP | 0 732 116 A2 | 9/1996 |
| EP | 0732116 A2 | 9/1996 |
| EP | 0 796 631 A2 | 9/1997 |
| EP | 0 865 798 A2 | 3/1998 |
| EP | 0 842 672 A2 | 5/1998 |
| EP | 0 845 276 A2 | 6/1998 |
| EP | 0 922 465 A2 | 6/1999 |
| EP | 0922465 A2 | 6/1999 |
| EP | 0 935 971 A2 | 8/1999 |
| EP | 1 119 386 B1 | 8/2001 |
| EP | 1 125 595 A1 | 8/2001 |
| EP | 1 800 706 A1 | 6/2007 |
| EP | 3 238 767 A1 | 11/2011 |
| GB | 1 529 190 | 10/1978 |
| GB | 2 111 394 A | 7/1983 |
| GB | 2 205 499 A | 12/1988 |
| GB | 2 298 797 A | 9/1996 |
| GB | 2 317 342 A | 3/1998 |
| GB | 2 317 830 A | 4/1998 |
| GB | 2317830 A | 4/1998 |
| GB | 2 318 735 A | 5/1998 |
| GB | 2 319 478 A | 5/1998 |
| GB | 2318735 A | 5/1998 |
| GB | 2 321 854 A | 8/1998 |
| GB | 2321854 A | 8/1998 |
| GB | 2 323 289 A | 9/1998 |
| GB | 2 323 290 A | 9/1998 |
| GB | 2 323 291 A | 9/1998 |
| GB | 2 323 292 A | 9/1998 |
| GB | 2324737 A | 11/1998 |
| GB | 2334215 A | 8/1999 |
| GB | 2 359 996 A | 9/2001 |
| GB | 2371990 A | 8/2002 |
| GB | 2 405 588 A | 3/2005 |
| GB | 2 454 199 A | 5/2009 |
| GB | 2436294 B | 12/2009 |
| JP | 3-39169 A | 2/1991 |
| JP | 7-509154 A | 10/1995 |
| JP | 8-000547 A | 1/1996 |

(56) References Cited

FOREIGN PATENT DOCUMENTS

| | | | |
|---|---|---|---|
| JP | 09-505211 A | 5/1997 |
| JP | 10-118182 A | 5/1998 |
| JP | 10-179745 A | 7/1998 |
| JP | 10-216233 A | 8/1998 |
| JP | 10-263086 A | 10/1998 |
| JP | 10-277156 A | 10/1998 |
| JP | 10-314308 A | 12/1998 |
| JP | 10-323391 A | 12/1998 |
| JP | 10-328303 A | 12/1998 |
| JP | 11-128349 A | 5/1999 |
| JP | 11-192304 A | 7/1999 |
| JP | 11-206885 A | 8/1999 |
| JP | 2000-152995 A | 6/2000 |
| JP | 2003-511108 A | 3/2003 |
| JP | 2003-528701 A | 9/2003 |
| JP | 2005-535397 A | 11/2005 |
| JP | 2006-522623 A | 10/2006 |
| JP | 2007-533337 A | 11/2007 |
| JP | 2008-526393 A | 7/2008 |
| JP | 2008-541817 A | 11/2008 |
| TW | 200706196 A | 2/2007 |
| WO | 91/03207 A1 | 3/1991 |
| WO | 91/07201 A1 | 5/1991 |
| WO | 91/12845 A1 | 9/1991 |
| WO | 92/13587 A1 | 8/1992 |
| WO | 94/02191 A1 | 2/1994 |
| WO | 95/06492 A1 | 3/1995 |
| WO | 95/33506 A1 | 12/1995 |
| WO | 97/12640 A1 | 4/1997 |
| WO | 97/12641 A1 | 4/1997 |
| WO | 98/16273 A1 | 4/1998 |
| WO | 98/50096 | 11/1998 |
| WO | 99/06093 A1 | 2/1999 |
| WO | 00/09189 | 2/2000 |
| WO | 00/20062 A2 | 4/2000 |
| WO | 00/22985 | 4/2000 |
| WO | 00/23135 | 4/2000 |
| WO | 00/61212 | 10/2000 |
| WO | 01/24860 A | 4/2001 |
| WO | 01/74431 A2 | 10/2001 |
| WO | 02/32490 A2 | 4/2002 |
| WO | 2004/016308 A2 | 2/2004 |
| WO | 2004/030527 A1 | 4/2004 |
| WO | 2004/089453 | 10/2004 |
| WO | 2005/011784 A1 | 2/2005 |
| WO | 2005/023350 A1 | 3/2005 |
| WO | 2005/058394 A1 | 6/2005 |
| WO | 2006/026237 A1 | 3/2006 |
| WO | 2006/037626 A2 | 4/2006 |
| WO | 2006/074515 A1 | 7/2006 |
| WO | 2006/125986 A1 | 11/2006 |
| WO | 2006/125987 A1 | 11/2006 |
| WO | 2006/125989 A1 | 11/2006 |
| WO | 2007/131267 A1 | 11/2007 |
| WO | 2009/156949 A2 | 12/2009 |
| WO | 2010/060224 A1 | 6/2010 |
| WO | 2010/100419 A1 | 9/2010 |
| WO | 2012/061869 A1 | 5/2012 |
| WO | 2013066195 A1 | 5/2013 |

OTHER PUBLICATIONS

M.O. Abdelatti, A cuff pressure controller for tracheal tubes and laryngeal mask airways; Blackwell Science Ltd, 1999, Anaesthesia, 1999, 54, pp. 981-985.
Jonathan L. Benumof, M.D., Laryngeal Mask Airway and the ASA Difficult Airway Algorithm, Medical Intelligence Article, Editor Dennis M. Fisher, M.D., Anesthesiology, V 84, No. 3, pp. 15, (c) 1996 American Society of Anesthesiologists. Inc. Lippincott-Raven Publishers, Date: Mar. 1996.
F. Engbers, Practical use of 'Diprifusor' systems, Blackwell Science Ltd. Anaesthesia, vol. 53, Supplement 1, pp. 28-34, Date 1998.
Lars I. Eriksson, M.D. et al., Functional Assessment of the Pharynx at Rest and during Swallowing in Partially Paralyzed Humans, Simultaneous Video manometry and Mechanomyography of Awake Human Volunteers, American Society of Anesthesiology, Inc., Anesthesiology, vol. 87, No. 5, pp. 1035-1042, Date Nov. 1997.
Gerald Burgard, MD, et al., The Effect of Laryngeal Mask Cuff Pressure on Postoperative Sore Throat INcidence, Journal of Clinical Anesthesia, vol. 8, pp. 198-201, Elsevier Science Inc, New York, NY, Date May 1996.
Robert A Caplan, M.D., et al., Adverse Respiratory Events in Anesthesia: A Closed Claims Analysis, Anesthesiology, vol. 72, No. 5, pp. 828-833, Date May 1990.
Donald E. Craven, MD., Prevention of Hospital-Acquired Pneumonia: Measuring Effect in Ounces, Pounds, and Tons, Annals of Internal Medicine, vol. 122, No. 3, pp. 229-231, Date Feb. 1, 1995.
LogoMed, Cuff-Pressure-Control CDR 2000, pp. 4.
P.R.F. Davies, et al., Laryngeal mask airway and tracheal tube insertion by unskilled personnel, The Lancet, Clinical Practice, vol. 336, pp. 977-979, Date Oct. 20, 1990.
W.F. De Mello, et al., The use of the laryngeal mask airway in primary anaesthesia, Correspondence, pp. 793-794, Retrieve date: 2001.
D. John Doyle Md PhD FRCPS, et al., Intraoperative Awareness: A Continuing Clinical Problem, Educational Synopses in Anesthesiology and Criticdal care Medicine, The Online Journal of Anesthesiology, vol. 3, No. 6, http://doyle.ibme.utoronto.ca/anesthesia/aware.htm, pp. 1-8, Date Jun. 1996.
Jonathan L. Benumof, M.D., Management of the Difficult Adult Airway with Special Emphasis on Awake Tracheal Intubation, Medical Intelligence Article, Editor Julien F. Biebuyck M.B., Anesthesiology, V 75, No. 6, pp. 1087-1110, Date Dec. 1991.
William N. Bernhard, M.D., Adjustment of Intracuff Pressure of Prevent Aspiration, The American Society of Anesthesiologists, Inc., Anesthesiology vol. 50, No. 4, p. 363-366, Date Apr. 1976.
William N. Bernhard, M.D. et al., Physical Characteristics of and Rates of Nitrous Oxide Diffusion into Tracheal Tube Cuffs, The American Society of Anesthesiologists, Inc., Anesthesiology, vol. 48, No. 6, p. 413-417, Date Jun. 1979.
A.I.J. Brain, et al., The laryngeal mask airway Development and preliminary trails of a newtype of airway, The Association of Anesesthetists of Gr. Britain and Ireland, Anaesthesia, vol. 40, p. 356-361, Date 1985.
A.I.J. Brain, The laryngeal mask airway—a possible new solution to airway problems in the emergency situation, Archives of Emergency Medicine, Case Report, 1, pp. 229-232, Date 1984.
A.I.J. Brain, The Laryngeal Mask—A New Concept in Airway Management, The Macmillan Press Ltd., British Jouranl of Anaesthesia, vol. 55, pp. 801-805, Date 1983.
A.I.J. Brain, et al., A new laryngeal mask prototype, Preliminary evaluation of seal pressures and glottic isolation, The Association ofAnaesthetists of Great Britain and Ireland, Anaesthesia, vol. 50, pp. 42-48, Date 1995.
A.I.J. Brain, Three cases of difficult intubation overcome by the laryngeal mask airway, The Association of Anaesthetists of Great Britain and Ireland, Case Report, Anaesthesia, vol. 40, pp. 353-355, Date 1985.
J. Brimacombe, The split laryngeal mask airway, Correspondence, Royal Perth Hospital, Perth 6001, Western Australia, p. 1. Date 1993.
P.M. Brodrick, et al., The laryngeal mask airway A study of 100 patients during spontaneous breathing, The Association of Anaesthetists of Gt. Britain and Ireland, Anaesthesia, vol. 44, pp. 238-241, Date 1989.
J.B. Glen, The development of 'Diprifusor': a TCI system for propofol, Blackwell Science Ltd., Anaesthesia, vol. 53, Supplement 1, pp. 13-21, Date 1998.
J.M. Gray, et al., Development of the technology for 'Diprifusor' TCI systems, Balckwell Science Ltd, Anaesthesia, vol. 53, Supplement 1, pp. 22-27, Date 1998.
M.L. Heath, Endotracheal intubation throught the Laryngeal Mask—helpful when laryngoscopy is difficult or dangerous, European Journal of Anaesthesiology, Supplement 4, pp. 41-45, Date 1991.
Jitendran Muthuswamy et al., The Use of Fuzzy Integrals and Bispectral Analysis of the Electroencephalogram to Predict Move-

(56) References Cited

OTHER PUBLICATIONS ment Under Anesthesia, IEEE Transactions of Biomedical Engineering, vol. 46, No. 3, pp. 291-299, Date Mar. 1999.
K. Nagai, et al., Unilateral Hypoglossal nerve paralysis following the use of the laryngeal mask airway, Case Report, The Association of Anaesthetists of Gt. Britain and Ireland, Anaesthesia, vol. 49, pp. 603-604, Date 1994.
Lars J. Kangas, et al., Neurometric Assessment of Adequacy of Intraoperative Anesthetic, Medical Technology Brief, pp. 3, Date 1999.
Rainer Bockelen, Observations by a third party concerning the European Patent Application No. 99 947 765.6-2318, TBK Tiedtke—Buhling—Kinne & POartnet (GbR), pp. 1-4, Date Jan. 18, 2005.
R.I. Patel, et al., Tracheal tube cuff pressure, Changes during nitrous oxide anaesthesia following inflation of cuffs with air and saline, The Association of Anaesthetists of Gt Britain and ireland, Anaesthesia, vol. 39, pp. 862-864, Date 1984.
International Search Report; Written Opinion of the International Searching Authority; PCT/ISA/237 Of PCT/GB2006/001913, Date Aug. 28, 2006.
John H. Pennant, et al, Comparison ofteh Endotracheal Tube and Laryngeal Mask in Airway Management by Paramedical Pesonnel, International Anesthesia Research Society, Anesth Analg, vol. 74, pp. 531-534, Date 1992.
Lynne K. Pippin, et al., Long-term tracheal intubation practive in teh United Kingdom, Forum, Anaesthesia, vol. 38, pp. 791-795, Date 1983.
J. C. Raeder, et al, Tracheal tube cuff pressures, The effects of different gas mixtures, The Association of Anaesthetists of Gt. Britain and Ireland, Anaesthesia, vol. 40, pp. 444-447, Date 1985.
Tbk (Tiedtke—Buhling—Kinne & Partnet), Response to Complaint Matter No. 4b 0 440-05, In the Matter of LMA Deutschland GmbH Vs. AMBU (Deutschland) GmbH, pp. 1-47, Date Feb. 10, 2006.
Armin Rieger, et al, Intracuff Pressures Do Not Predict Laryngopharyngeal Discomfort after Use of the Laryngeal Mask Airway, American Society of Anesthesiologists, Inc., Lippincott-Raven Publishers, Anesthesiology, vol. 87, No. 1, pp. 63-67, Date Jul. 1997.
S. Hickey, et al., Cardiovascular response to insertion of Brain's laryngeal mask, The Association of Anaesthetists of Gt. Britain and Ireland, Anaesthesia, vol. 45, pp. 629-633, Date 1990.
Shinichi Inomata, M.D, et al., Transient Bilateral Vocal Cord Paralysis after Insertion of a Laryngeal Mask Airway, Case Report, American Society of Anesthesiologists, Inc., Anesthesiology, vol. 82, No. 3, pp. 787-788, Date Mar. 1995.
L. Jacobson et al., A study of Intracuff Pressure Measurements, Trends and Behaviour in Patients during Prolonged Periods of Tracheal Intubation, Macmillan Publishers Ltd, British Journal of Anaesthesia, 53, 97, pp. 97-101, Date 1981.
L. Worthington, et al, Prodeedings of the Anaesthetic Research Society, Leeds Meeting, British Journal of Anaesthesia, vol. 75, pp. 228-229, Date 1995.
J. Michael Wynn, M.D., et al, Tongue Cyanosis after Laryngeal Mask Airway Insertion, Correspondence, American Society of Anesthesiologists, Inc., Anesthesiology, vol. 80, No. 6, p. 1, Date Jun. 1994.
V. Kambic, et al., Intubation Lesions of the Larynx, British Journal of Anaesthesia, 50, Macmillan Journals Ltd, pp. 587-590, Date 1978.
L. Worthington, et al., Proceedings of the Anaesthetic Research Society, Leeds Meeting, British Journal of Anaesthesia, 75, pp. 228-229, Date Mar. 31-Apr. 1, 1995.
Carl-Eric Lindholm, Prolonged Endotracheal Intubation, ACTA Anaesthesiologica Scandinavica, Iussu Societatis Anaeshtesiologicae Scandinavicae Edita Supplementum XXXIII, pp. 19, Date 1969.
S. Majumder, et al., Bilateral Lingual nerve injury following the use of the laryngeal mask airway, Case Report, Anaesthesia, 53, pp. 184-186, Date 1998.

Todd Martin, Patentability of Methods of Medical Treatment: A Comparative Study, Journal of the Patent & Trademark Office Society, 82, pp. 381-423, Date Jun. 2000.
Merriam-Webster's Collegiate Dictionary, Tenth Edition, Convex, Saddle, Merriam-Webster, Incoporated, Springfield, Massachusetts, USA, pp. 4, Date 1997.
D.M. Miller, A pressure regulator for the cuff of a tracheal tube, The Association of Anaesthesia of Great Britan and Ireland, Anaesthesia, vol. 47, pp. 594-596, Date 1992.
R. D. Seegobin, et al., Endotracheal cuff pressure and tracheal mucosal blood flow; endoscopic study of effects of four large volume cuffs, British Medical Journal, vol. 288, pp. 965-968, Date Mar. 31, 1984.
B. A. Willis, et al, Tracheal tube cuff pressure, Clinical use of the Cardiff Cuff Controller, The Association of Anaesthetists of Gt. Britain and Ireland, Anaesthesia, vol. 43, pp. 312-314, Date 1988.
Joseph R. Brimacombe, Laryngeal Mask Anesthesia Principles and Practice, Second Edition, Chapter 1 History; ISBN 0/7020-2700-6; Elsevier Limited, pp. 50; Date 2005.
Joseph R. Brimacombe, Laryngeal Mask Anesthesia Principles and Practice, Second Edition, Chapter 2 Equipment; ISBN 0/7020-2700-6; Elsevier Limited, pp. 41-72; Date 2005.
Joseph R. Brimacombe, Laryngeal Mask Anesthesia Principles and Practice, Second Edition, Chapter 3 Anatomy; ISBN 0/7020-2700-6; Elsevier Limited, pp. 73-104; Date 2005.
Joseph R. Brimacombe, Laryngeal Mask Anesthesia Principles and Practice, Second Edition, Chapter 4 Pathophysiology; ISBN 0/7020-2700-6; Elsevier Limited, pp. 105-136; Date 2005.
Joseph R. Brimacombe, Laryngeal Mask Anesthesia Principles and Practice, Second Edition, Chapter 5 Equipment; ISBN 0/7020-2700-6; Elsevier Limited, pp. 137-152; Date 2005.
Joseph R. Brimacombe, Laryngeal Mask Anesthesia Principles and Practice, Second Edition, Chapter 6 Conduit to the respiratory and gastrointestinal tracts; ISBN 0/7020-2700-6; Elsevier Limited, pp. 153-176 ; Date 2005.
Joseph R. Brimacombe, Laryngeal Mask Anesthesia Principles and Practice, Second Edition, Chapter 7 Pre-anesthesia phase; ISBN 0/7020-2700-6; Elsevier Limited, pp. 177-190 ; Date 2005.
Joseph R. Brimacombe, Laryngeal Mask Anesthesia Principles and Practice, Second Edition, Chapter 8 Placement phase; ISBN 0/7020-2700-6; Elsevier Limited, pp. 191-240; Date 2005.
Joseph R. Brimacombe, Laryngeal Mask Anesthesia Principles and Practice, Second Edition, Chapter 9 Maintenance phase; ISBN 0/7020-2700-6; Elsevier Limited, pp. 241-264; Date 2005.
Joseph R. Brimacombe, Laryngeal Mask Anesthesia Principles and Practice, Second Edition, Chapter 10 Emergence phase; ISBN 0/7020-2700-6; Elsevier Limited, pp. 265-280; Date 2005.
Joseph R. Brimacombe, Laryngeal Mask Anesthesia Principles and Practice, Second Edition, Chapter 11 Resuscitation; ISBN 0/7020-2700-6; Elsevier Limited, pp. 281-296; Date 2005.
Joseph R. Brimacombe, Laryngeal Mask Anesthesia Principles and Practice, Second Edition, Chapter 12 Intensive care; ISBN 0/7020-2700-6; Elsevier Limited, pp. 297-304; Date 2005.
Joseph R. Brimacombe, Laryngeal Mask Anesthesia Principles and Practice, Second Edition, Chapter 13 Difficult airway; ISBN 0/7020-2700-6; Elsevier Limited, pp. 305-356; Date 2005.
Joseph R. Brimacombe, Laryngeal Mask Anesthesia Principles and Practice, Second Edition, Chapter 14 Pediatrics; ISBN 0/7020-2700-6; Elsevier Limited, pp. 357-390; Date 2005.
Joseph R. Brimacombe, Laryngeal Mask Anesthesia Principles and Practice, Second Edition, Chapter 15 Coexisting disease; ISBN 0/7020-2700-6; Elsevier Limited, pp. 391-410; Date 2005.
Joseph R. Brimacombe, Laryngeal Mask Anesthesia Principles and Practice, Second Edition, Chapter 16 Surgery; ISBN 0/7020-2700-6; Elsevier Limited, pp. 411-444; Date 2005.
Joseph R. Brimacombe, Laryngeal Mask Anesthesia Principles and Practice, Second Edition, Chapter 17 Flexible LMA for shared airway; ISBN 0/7020-2700-6; Elsevier Limited, pp. 445-468; Date 2005.
Joseph R. Brimacombe, Laryngeal Mask Anesthesia Principles and Practice, Second Edition, Chapter 18 Intubating LMA for airway intubation; ISBN 0/7020-2700-6; Elsevier Limited, pp. 469-504; Date 2005.

(56) References Cited

OTHER PUBLICATIONS

Joseph R. Brimacombe, Laryngeal Mask Anesthesia Principles and Practice, Second Edition, Chapter 19 ProSeal LMA for ventilation and airway protection; ISBN 0/7020-2700-6; Elsevier Limited, pp. 505-538; Date 2005.

Joseph R. Brimacombe, Laryngeal Mask Anesthesia Principles and Practice, Second Edition, Chapter 20 Educational considerations; ISBN 0/7020-2700-6; Elsevier Limited, pp. 539-550; Date 2005.

Joseph R. Brimacombe, Laryngeal Mask Anesthesia Principles and Practice, Second Edition, Chapter 21 Problems; ISBN 0/7020-2700-6; Elsevier Limited, pp. 551-576; Date 2005.

Joseph R. Brimacombe, Laryngeal Mask Anesthesia Principles and Practice, Second Edition, Chapter 22 Other extraglottic airway devices; ISBN 0/7020-2700-6; Elsevier Limited, pp. 577-632; Date 2005.

Joseph R. Brimacombe, Laryngeal Mask Anesthesia Principles and Practice, Second Edition, Appendix A: Stop press I; Appendix B: Strop press II, and Appendix C: List of Researchers; ISBN 0/7020-2700-6; Elsevier Limited, pp. 632-673; Date 2005.

International Standard, Anaesthetic and respiratory equipment—Supralaryngeal airways and connectors; ISO 11712, First Edition, Published in Switzerland; pp. 36; Date May 15, 2009.

Joseph R. Brimacombe, Chapter 3, Anatomy, Laryngeal Mask Anesthesia Principles and practice, Second Edition, Saunders Aan imprint of Elsevier Limited; ISBN 0/7020-2700-6, Printed in China, pp. 32, Date: 2005.

Donald M. Miller, A Proposed Classification and Scoring System for Supraglottic Sealing Airways; A Brief Review; General Articles Medical Intelligence, International Anesthesia Research Society 0003-2999, Anesth Analg; pp. 1553-1159; Date: 2004.

Jonathan L. Benumof, M.D., The Glottic Aperture Seal Aiway, A New Ventilatory Device, Anesthesiology, American Society of Anesthesiologists, Inc., Lippincott-Raven Publishers, vol. 88, No. 5, pp. 1219-1226, Date: May 1998.

A.I.J. Brain, et al., A new laryngeal mask prototype, Preliminary evaluation of seal pressures and glottic isolation, The Association of Anaesthetists of Gt Britain and Ireland, Anaesthesia, vol. 50, pp. 42-48, Date 1995.

C. Verghese, J. et al., Clinical assessment of the single use laryngeal mask airway—the LMA-Unique, British Journal of Anaeshtesia, 80, pp. 677-679, Date 1998.

John W.R. McIntyre MD FRCPC, History of Anaesthesia, Oropharyngeal and nasopharyngeal airways: I (1880-1995), Canadian Journal Of Anaesthesia, 43:6, p. 629-635, Date 1996.

Hiroshi Ishimura, M.D., et al., Impossible Insertion of the Laryngeal Mask Airway and Oropharyngeal Axes, Case Reports, American Society of Anesthesiologists, Inc., Anesthesiology, V. 83, No. 4, Lippincott-Raven Publishers, pp. 867-869, Date Oct. 1995.

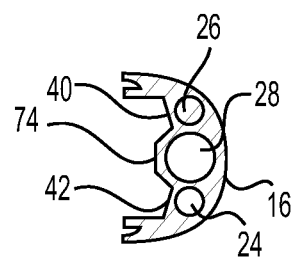
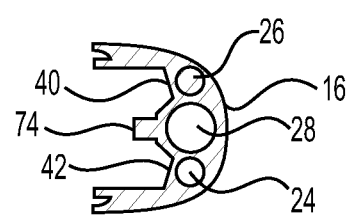
FIG. 54    FIG. 55
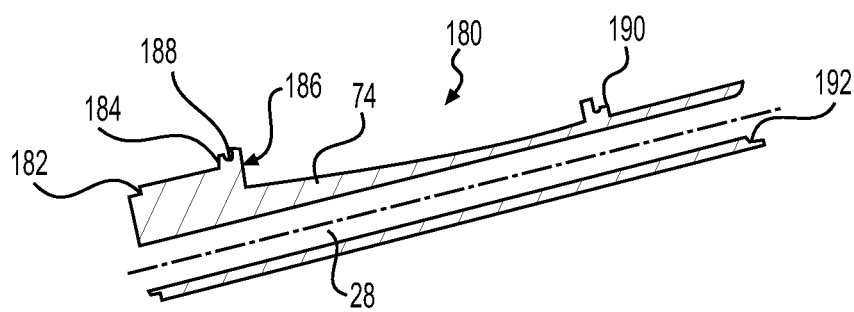
FIG. 53
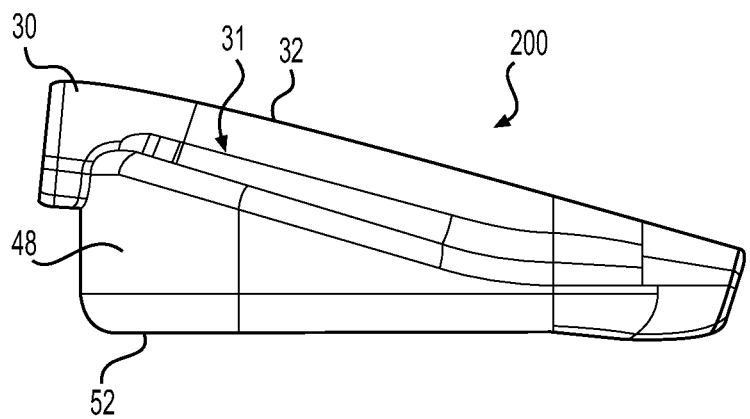
FIG. 56

ARTIFICIAL AIRWAY

CROSS REFERENCE TO RELATED APPLICATIONS

This application is a continuation of U.S. application Ser. No. 13/382,733, filed Mar. 26, 2012, which is a National Stage of International Application No. PCT/AU2010/000861 filed Jul. 6, 2010, claiming priority based on Australian Patent Application No. 2009903153 filed Jul. 6, 2009, the disclosures of which are incorporated herein in their entirety by reference.

FIELD OF THE INVENTION

This invention relates to an artificial airway which can be used in surgical procedures or in emergencies to establish an uninterrupted airway to the lungs of a patient.

BACKGROUND OF THE INVENTION

In recent years the use of supraglottic airways has become widespread. Most of the devices include an airway tube having an inflatable cuff mounted at the distal end. The cuff includes a recess which is in fluid communication with the airway tube to allow anaesthetic gas to be administered to the lungs of a patient, or alternatively in an emergency situation to allow air to pass in an unobstructed way to the lungs of a patient.

It is desirable that the artificial airway should form a good seal around the glottic opening of the patient. This has the advantage that substantially all of the anaesthetic gas supplied through the airway passes to the lungs of the patient. Further, the seal helps to prevent any regurgitated material entering the lungs of the patient.

In some known devices an evacuation tube is provided so as to communicate with the oesophagus of the patient so that any regurgitated material can be vented through the evacuation tube, thereby minimising the possibility that the regurgitated material enters the lungs of the patient. Normally suction is applied to the evacuation tube to facilitate this process as disclosed in AU-B-52036/90 for example.

SUMMARY OF THE INVENTION

The general object of the invention is to provide an improved artificial airway 30 which has improved performance and which is inexpensive to manufacture.

According to a first aspect of the invention there is provided an artificial airway including:
an airway tube including at least one airway conduit;
an inflatable cuff mounted on a distal end of the tube;
a support member extending into the cuff, the cuff having inner side walls, anterior walls and a posterior wall, the inner side walls being joined to the support member to define a recess which communicates with the airway conduit, the anterior walls and posterior wall, sealingly engaging, in use, about the glottic opening and posterior pharyngeal wall respectively of a patient.

Preferably, the support member is integral with the airway tube.

Preferably further, the support member defines a posterior wall of the recess.

The invention also provides an artificial airway including:
an airway tube having at least one airway conduit therein;
an inflatable cuff mounted on a distal end of the airway tube, an end portion of the airway tube extending into the cuff, the cuff including a recess which is defined by the end portion of the airway tube and inner sidewalls of the cuff which are sealingly connected to said end portion and wherein said at least one airway conduit is in fluid communication with said recess;

the cuff including an anterior sealing wall which merges from the inner sidewalls, the anterior sealing wall lying generally in a plane and, in use, sealingly engages the glottic opening of a patient; the cuff further including a posterior wall extending from outer peripheral parts of the anterior sealing wall to extend over said end portion and, in use, being resiliently extended, on inflation of the cuff, to sealingly engage the posterior pharyngeal wall of the patient.

Preferably the anterior sealing wall is only connected to said end portion of the airway adjacent to the distal and proximal ends thereof.

Preferably further, the shape of the cuff is such, that when inflated and in a lateral cross-section section which includes a recess, the posterior wall has an inverted U-shape, the ends of which merge into the outer peripheral parts of the anterior sealing wall and wherein the cuff is spaced from the end portion of the airway tube except where the inner sidewalls thereof are connected to said end portion.

Preferably further, the inflatable cuff is integrally moulded from silicon rubber.

In accordance with another aspect the invention provides an artificial airway including:
an airway tube having at least one airway conduit therein;
a cuff mounted on a distal end of the tube and having a recess which is in fluid communication with the airway conduit;
an evacuation chamber located at a distal end of the cuff, the chamber, in use, being located adjacent to the upper oesophageal sphincter of a patient;
an evacuation conduit in fluid communication with the evacuation chamber; and
a ventilation conduit in fluid communication with the evacuation chamber, the arrangement being such that, in use, suction is applied to the evacuation conduit whereby regurgitated material entering the evacuation chamber is removed through evacuation conduit and wherein the ventilation conduit substantially prevents a negative pressure being applied to the tissue of the patient.

Preferably, the ventilation conduit vents the evacuation chamber to atmosphere.

In this embodiment, there is localised suction at the point where the evacuation conduit opens into the evacuation chamber but because the chamber is vented to atmosphere the pressure at the distal edge of the chamber is atmospheric or only slightly negative thereby avoiding the possibility that the distal edge of the chamber is sucked into contact with the mucosa adjacent to the upper oesophageal sphincter. In this way damage to the mucosa is substantially avoided. Also if negative pressure is applied continuously to the oesophagus there is a possibility that regurgitation could be encouraged which is undesirable.

The invention also provides an artificial airway comprising:
an airway tube having at least one airway conduit therein;
an inflatable cuff mounted on a distal end of the airway tube, an end portion of the airway tube extending into the cuff, the cuff including a recess which is defined by the end portion of the airway tube and inner sidewalls of the cuff which are sealingly connected to said end portion and wherein said at least one airway conduit is in fluid communication with said recess;

the cuff including an anterior sealing wall which merges from the inner sidewalls, the anterior sealing wall lying generally in a plane and, in use, sealingly engages the glottic opening of a patient; the cuff further including a posterior wall extending from outer peripheral parts of the anterior sealing wall to extend over said end portion and, in use, being resiliently extended, on inflation of the cuff, to sealingly engage the posterior pharyngeal wall of the patient;

a connector body for providing fluid communication with said at least one airway conduit; and means for sealingly connecting the connector body to the proximal end of the airway tube.

The invention also provides an artificial airway including:

an airway tube having at least one airway conduit therein;

an inflatable cuff mounted on a distal end of the airway tube, an end portion of the airway tube extending into the cuff, the cuff including a recess which is defined by the end portion of the airway tube and inner sidewalls of the cuff which are sealingly connected to said end portion and wherein said at least one airway conduit is in fluid communication with said recess;

the cuff including an anterior sealing wall which merges from the inner sidewalls, the anterior sealing wall lying generally in a plane and, in use, sealingly engages the glottic opening of a patient; the cuff further including a posterior wall extending from outer peripheral parts of the anterior sealing wall to extend over said end portion and, in use, being resiliently extended, on inflation of the cuff, to sealingly engage the posterior pharyngeal wall of the patient;

an evacuation chamber located at a distal end of the cuff, the chamber, in use, being located adjacent to the upper oesophageal sphincter of a patient;

an evacuation conduit in fluid communication with the evacuation chamber; and an evacuation chamber vent conduit in fluid communication with the evacuation chamber;

and wherein at least the evacuation conduit and the ventilation conduit are located within said distal end of the airway tube.

The invention also provides an artificial airway including:

an airway tube having at least one airway conduit therein;

an inflatable cuff mounted on a distal end of the airway tube, an end portion of the airway tube extending into the cuff, the cuff including a recess which is defined by the end portion of the airway tube and inner sidewalls of the cuff which are sealingly connected to said end portion and wherein said at least one airway conduit is in fluid communication with said recess;

the cuff including an anterior sealing wall which merges from the inner sidewalls, the anterior sealing wall lying generally in a plane and, in use, sealingly engages the glottic opening of a patient; the cuff further including a posterior wall extending from outer peripheral parts of the anterior sealing wall to extend over said end portion and, in use, being resiliently extended, on inflation of the cuff, to sealingly engage the posterior pharyngeal wall of the patient;

characterised in that the cuff is moulded as single integral moulding.

International Publication No. WO 00/09189 discloses a typical prior art airway which has provision for drainage of the oesophagus. In this device there is a main cuff, back plate and a separate back cuff which are mounted to the distal ends of various tubes. In comparison, the device of the invention essentially eliminates the back plate as a separate component because, from a functional point of view, the end portion of the airway tube provides the necessary rigidity to this part of the device. Also, in the prior art device the main cuff is formed as an inflatable torus of asymmetrical oval or elliptical shape which is separately moulded from the back cuff. In contrast, in preferred embodiments of the invention, the airway does not have these components separately formed. There are no toroidal or annular inflatable rings in the device. The unitary cuff of the invention is moulded as a single component which has parts which sealingly engage about the glottic opening and the posterior pharyngeal wall of the patient. This effectively eliminates one of the components of the mask (the back plate) and furthermore makes the assembly process much simpler because the back plate and back cuff do not need to be separately moulded and then bonded to the main cuff.

The invention will now be further described with reference to the accompanying drawings.

BRIEF DESCRIPTION OF THE DRAWINGS

FIG. 53 is a schematic longitudinal sectional view along the line 53-53;

FIG. 54 is a cross-sectional view along the line 54-54;

FIG. 55 is a cross-sectional view along the line 55-55;

FIG. 56 is a side view of an inflatable cuff of the second embodiment;

DETAILED DESCRIPTION OF THE PREFERRED EMBODIMENTS

Figure 3:
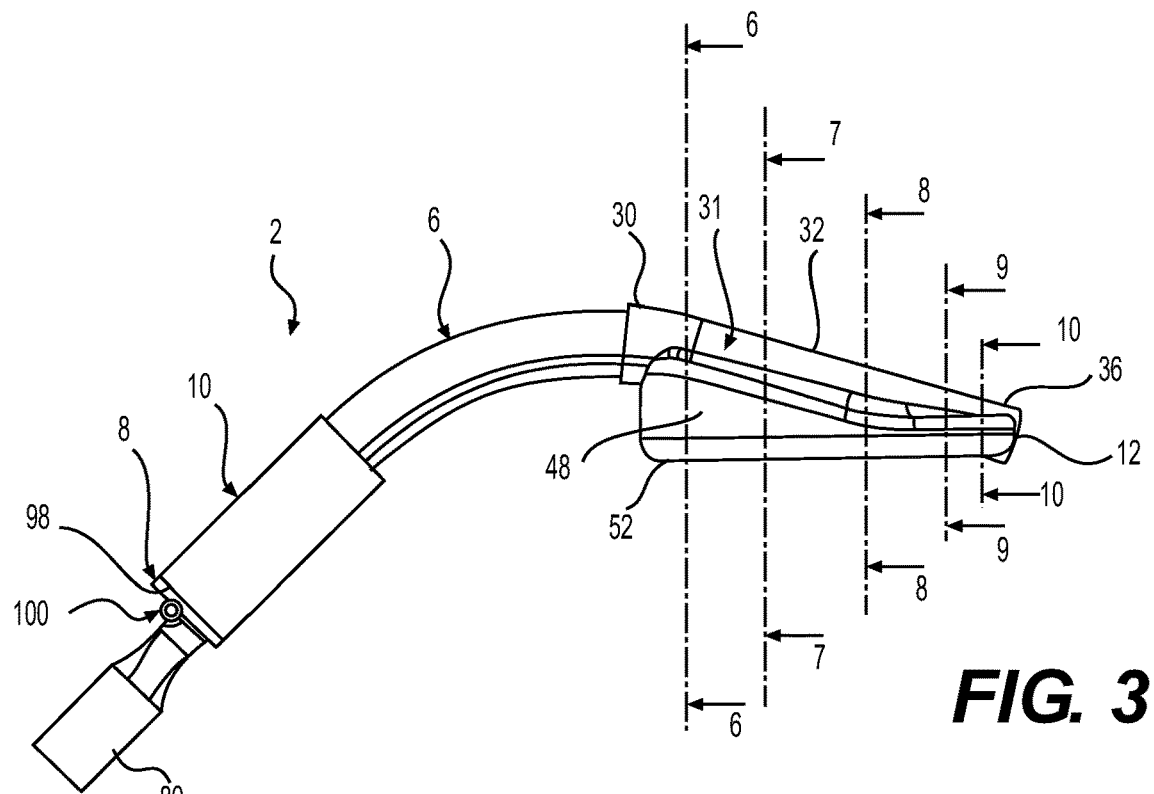
FIG. 3 is a side view of the airway.
Figure 4:
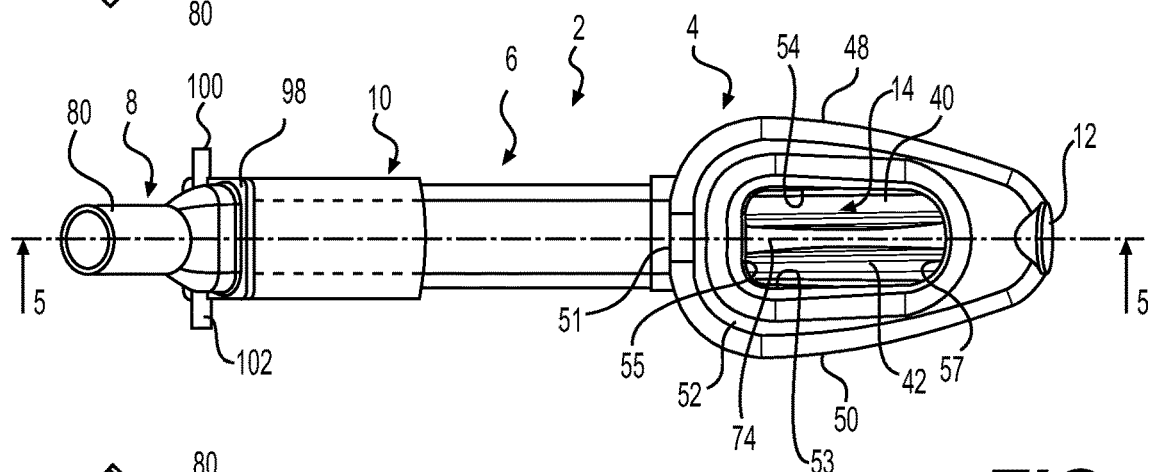
FIG. 4 is a plan view showing the anterior side of the airway.

FIGS. 1 to 10 show an artificial airway 2 constructed in accordance with the invention. The artificial airway 2 in the illustrated arrangement is assembled from four components: an inflatable cuff 4, airway tube 6, connector body 8 and joining sleeve 10. In FIGS. 1 to 10, the inflatable cuff 4 is shown in an uninflated position. As best seen in FIG. 3, the cuff 4 has a generally wedge shape as seen in side view. It has however an evacuation chamber 12 at its distal end. As best seen in FIG. 4 the cuff also has a generally wedge shape when viewed in plan except that it is somewhat truncated at its distal end where the evacuation chamber 12 is located. As the cuff includes a recess 14 which communicates with conduits in the airway tube 6 to permit an anaesthetic gas or air to be administered to the lungs of a patient, as will be described in more detail below.

Figure 6:
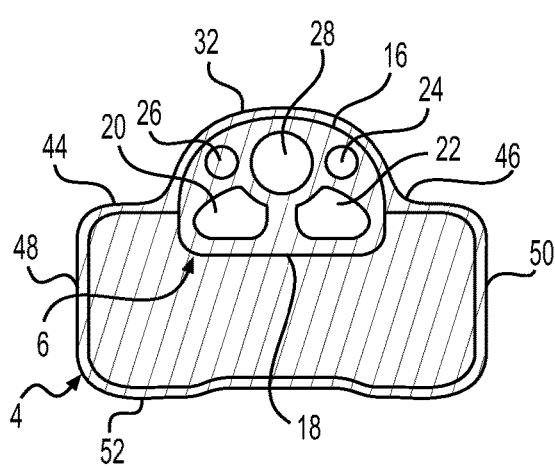
FIG. 6 is a cross-sectional view along the line 6-6.

The cross-sectional view of FIG. 6 shows the cross-sectional configuration of the airway tube 6. It will be seen that it is generally D-shaped in cross-section having a curved posterior side 16 and generally flat anterior side 18. The airway tube 6 includes two airway conduits 20 and 22 which convey anaesthetic gas or air to the recess 14, as will be described in more detail below. The airway tube 6 includes an inflation conduit 24 which is in fluid communication with the interior of the cuff 4 to enable inflation thereof. The airway tube 6 further includes an evacuation conduit 26, the distal end of which is in fluid communication with the interior of the evacuation chamber 12. The airway tube 6 further includes an evacuation chamber vent conduit 28 which also opens to the interior of the evacuation chamber 12.

Figure 1:
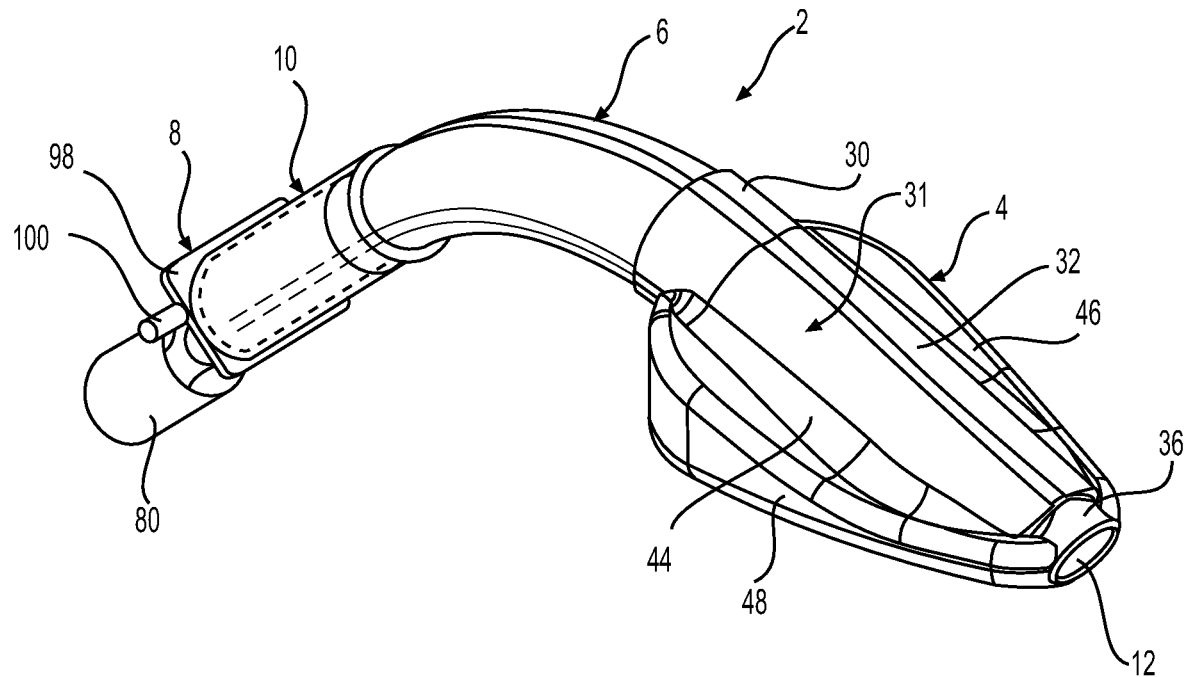
FIG. 1 is an isometric view of an airway device of the invention showing the posterior side thereof.
Figure 2:
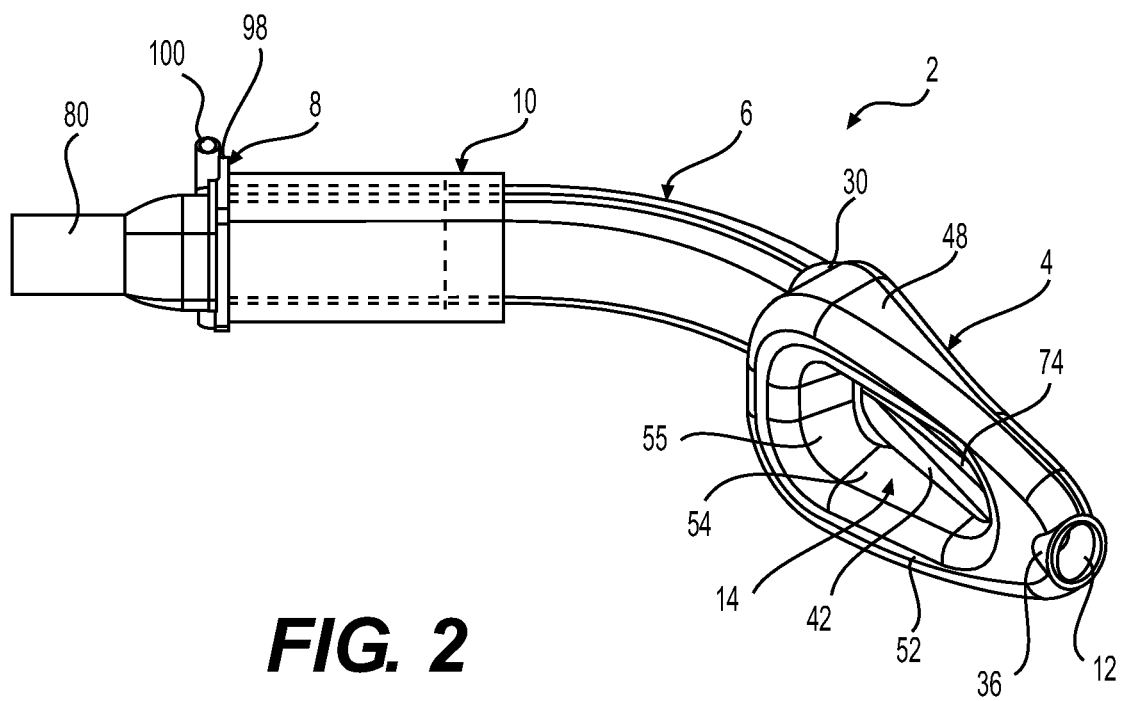
FIG. 2 is an isometric view of an airway showing the anterior side of the cuff.
Figure 5:
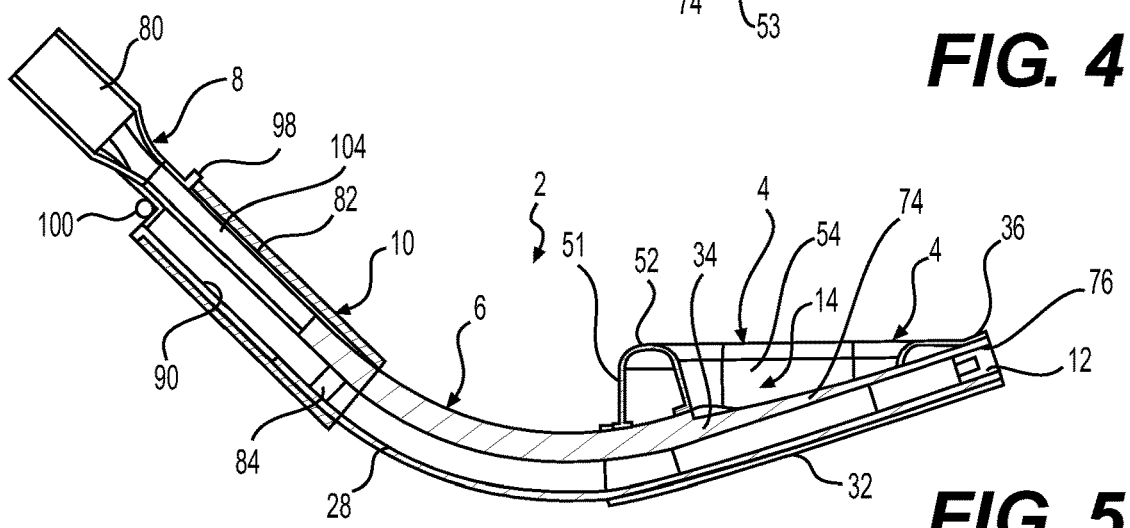
FIG. 5 is a longitudinal cross-sectional view along the line 5-5.

The cuff includes a proximal connecting spigot 30 which is of complementary shape to the airway tube 6. The spigot 30 is bonded to the outer surface of the airway tube by means of silicon adhesive so as to form a gas-tight seal therewith. The posterior wall 31 of the cuff 4 is a generally semi-cylindrical portion 32 which is contiguous with the adjacent part of the spigot 30, as best seen in FIG. 1. The portion 32 accommodates the distal end portion 34 of the tube 6 which enters the cuff 4 as best seen in FIG. 5. The distal end of the cuff is formed with a distal spigot 36 which is bonded to the adjacent part of the airway tube 6. The interior of the spigot 36 defines the evacuation chamber 12.

The airway tube 6 is formed with two longitudinally extending airway openings 40 and 42 which communicate with the airway conduits 20 and 22 respectively so as to permit anaesthetic gas to pass into the recess 14. It will be appreciated from FIG. 7 that the conduits 24, 26 and 28 are not in fluid communication with the recess 14.

Figure 7:
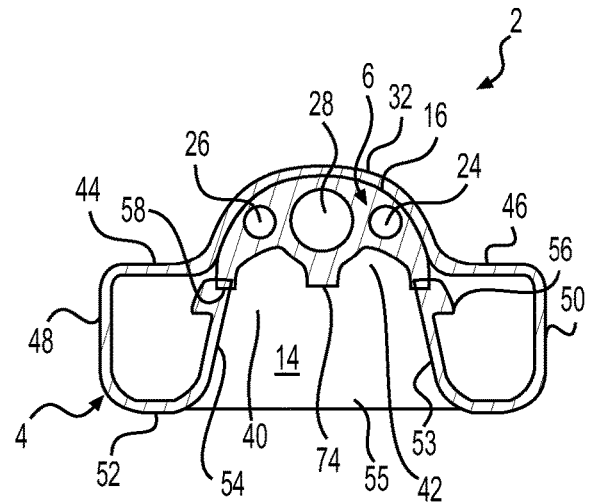
FIG. 7 is a cross-sectional view along the line 7-7.
Figure 8:
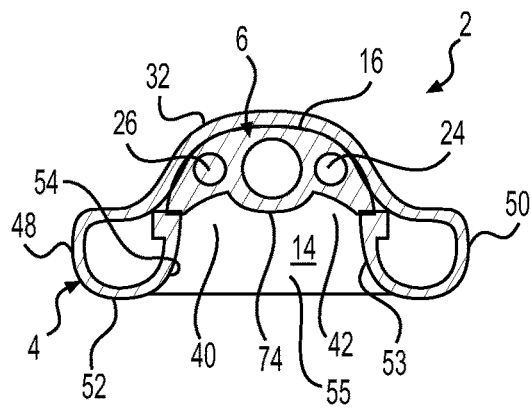
FIG. 8 is a cross-sectional view along the line 8-8.

The posterior wall 31 of the cuff includes two laterally extending lobes 44 and 46 which extend laterally from the semi-cylindrical portion 32 and generally extend from the proximal spigot 30 and the distal spigot 36. The cuff includes lateral sidewalls 48 and 50 which extend downwardly from the lobes 44 and 46 and merge into an anterior sealing wall 52. As best seen in FIGS. 6 and 7, the anterior sealing wall 52 is generally flat, that is to say lies within a single plane. The cuff includes a proximal end wall 51, the edges of which merge into the lateral sidewalls 48 and 50 and the sealing wall 52 In use the anterior sealing wall 52 seals about the epiglottic opening of a patient, as will be described in more detail below. The cuff includes lateral inner sidewalls 53 and 54 which merge upwardly from the anterior sealing wall 52 to define the lateral parts of the recess 14. The cuff also includes proximal and distal inner sidewalls 55 and 57 which also merge upwardly from anterior sidewall 52 to define the end parts of the recess 14. The upper periphery of the inner sidewalls 53, 54, 55 and 57 are formed with a rim 56 which includes a rebate 58 at its inner edge. The rebate 58 is shaped so as to be complementary to the anterior edge of the airway tube 6 adjacent to the openings 40 and 42. Silicon bonding agent is used to bond the rim 56 to the adjacent edges of the airway tube 6 so that the entire upper periphery of the inner sidewalls 54 is bonded so as to form a gas-tight seal therewith.

It will be appreciated that the cuff is joined to the end portion 34 of the airway 6 only at the spigots 30 and 34 and the upper periphery of the sidewalls 54 as described above.

Figure 9:
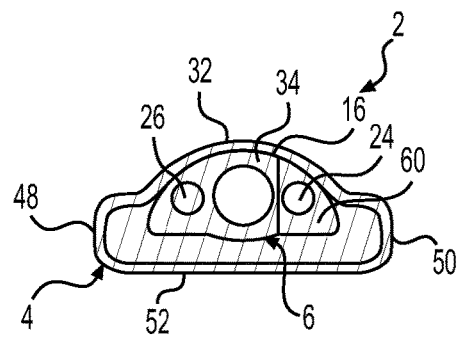
FIG. 9 is a cross-sectional view along the line 9-9.
Figure 10:
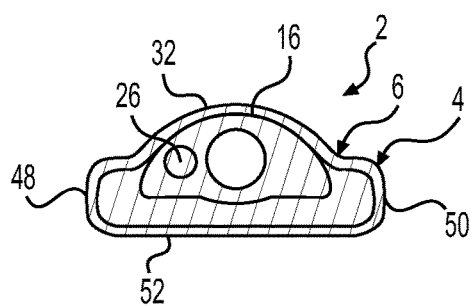
FIG. 10 is a cross-sectional view along the line 10-10.

As best seen in FIG. 9, the end portion 34 of the airway tube 6 includes a notch 60 which communicates with the inflation conduit 24 so as to permit the cuff 4 to be inflated.

Figure 11:
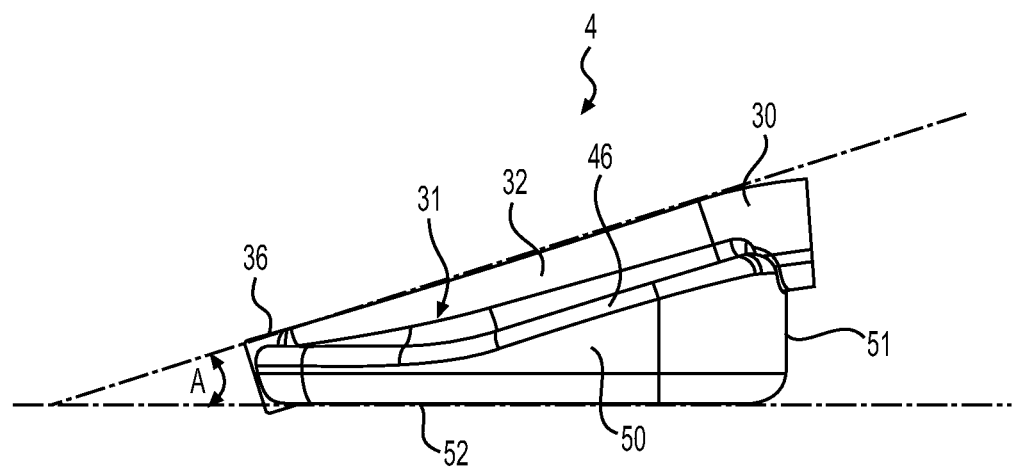
FIG. 11 is a side view of the cuff.
Figure 12:
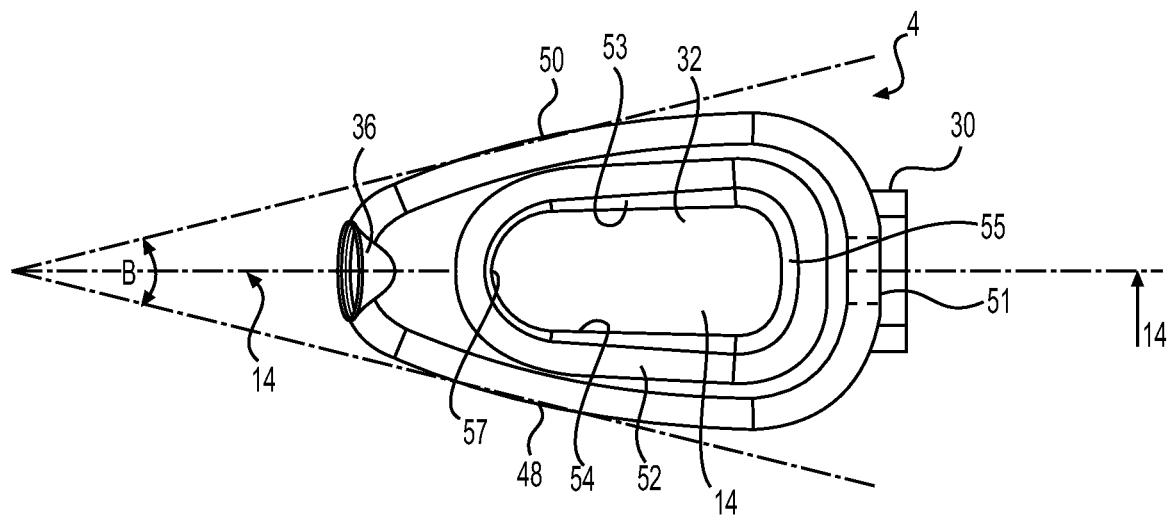
FIG. 12 is a plan view showing the anterior side of the cuff.
Figure 13:
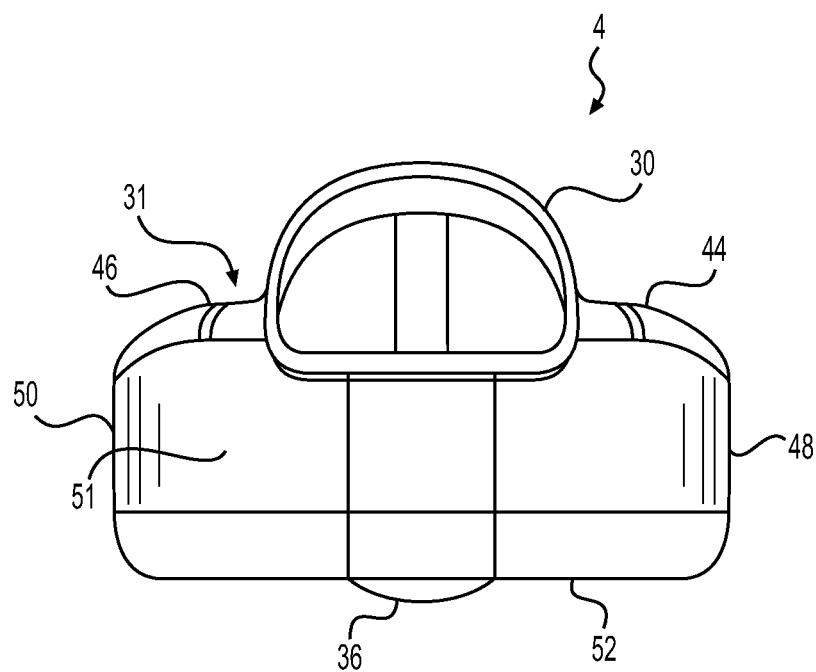
FIG. 13 is an end view of the cuff.
Figure 14:
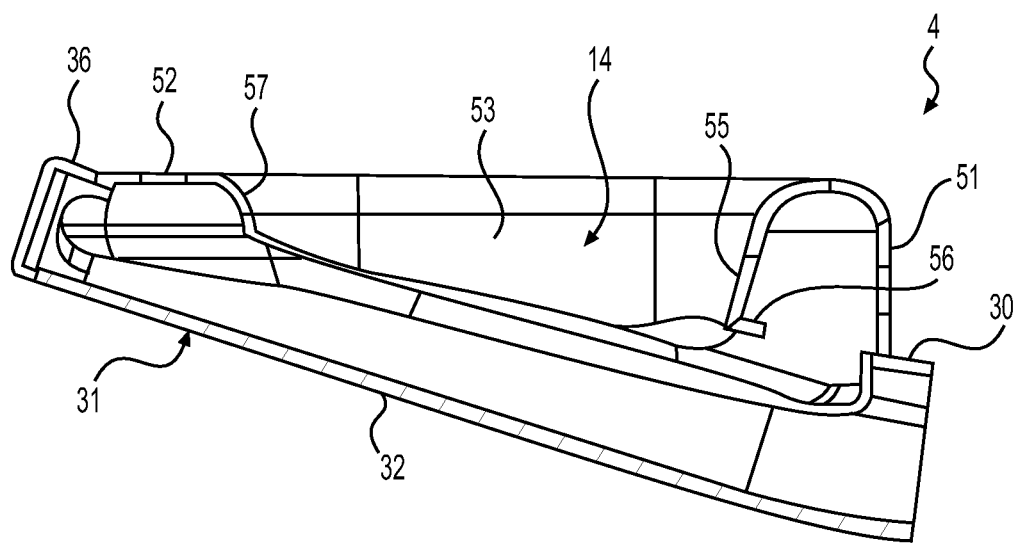
FIG. 14 is a cross-sectional view along the line 14-14.
Figure 15:
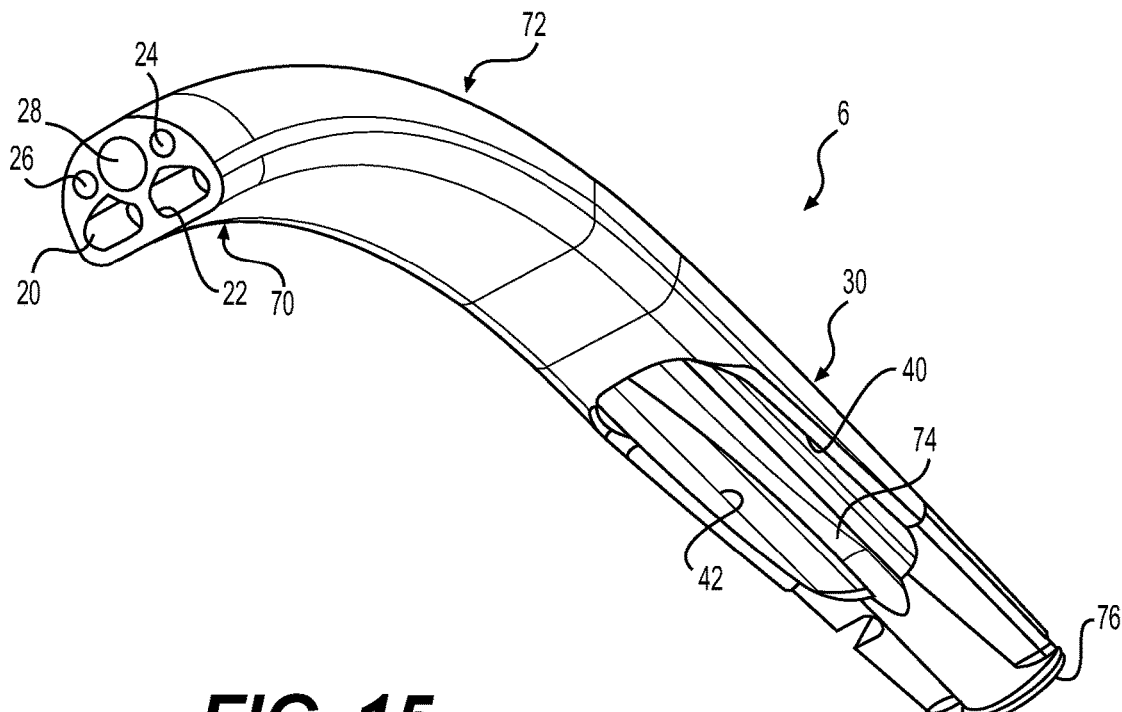
FIG. 15 is an isometric view of the airway tube.
Figure 16:
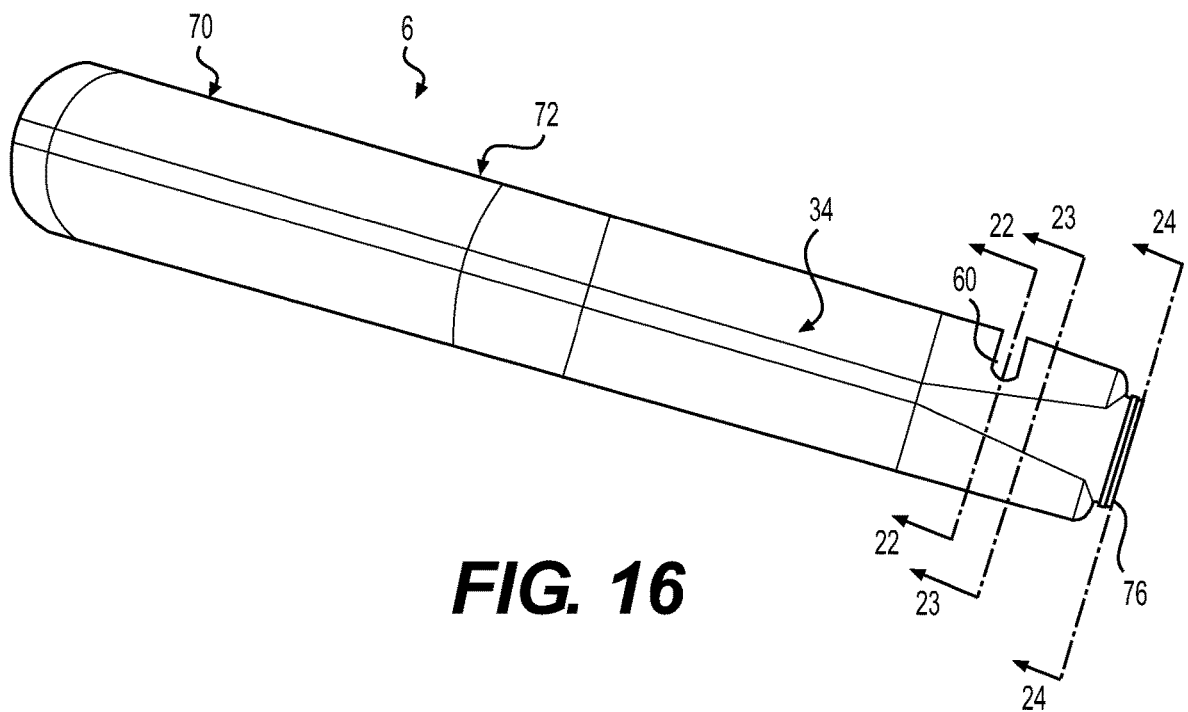
FIG. 16 is a view of the posterior side of the airway tube.

FIGS. 11 to 13 show the cuff 4 prior to bonding to the end portion 34 of the airway tube 6. The cuff is preferably injection moulded from silicon rubber having a Shore A hardness in the range 25 to 40. The wall thickness is preferably in the range from 1 to 2 mm. In the illustrated embodiment, the wall thickness is uniform and is approximately 1 mm in thickness. Alternatively, the wall thickness could be varied in order to produce differential expansions when inflated and in this case the wall thickness would be about 1 mm in thickness at the thinner parts and about 2 mm at the wider parts. Where wall thickness variation is employed, the wall thickness could be thicker in the walls which define the anterior sealing wall 52 and the inner sidewalls 53, 54, 55 and 57 and proximal end wall 51 so that these walls tend to maintain their shape during inflation. The lateral sidewalls 48, 50 and the posterior wall 31 are preferably thinner so that these walls expand to a greater extent during inflation.

As mentioned above, the cuff is generally wedge-shaped when viewed from the side, as shown in FIG. 11. The apex angle A is preferably 15° to 25° and preferably 20°.

The cuff is also generally wedge-shaped when viewed in plan, as seen in FIG. 12, except that the apex is truncated, where the spigot 36 is located. The apex angle B is preferably in the range from 20° to 30° and most preferably about 22.5°. It will also be seen that the sidewalls 48 and 50 when viewed in plan are relatively straight or have only a very slight curve.

It will also be noted that the recess 14 is of a rectangular shape when viewed in plan as seen in FIG. 12. Further, the inner sidewalls 53, 54, 55 and 57 are inclined inwardly towards to the rim 56 at an angle of about 15°.

In one embodiment, the length of the cuff 4 as measured in the longitudinal direction is approximately 93 mm and the widest portion, that is to say between the lateral sidewalls 46 and 48, is about 50 mm. The height of the sidewall 48 varies from about 8 mm at the distal end of the cuff to about 20 mm at the proximal end. The distance from the anterior sealing wall 52 to the highest point on the cylindrical portion 32 is about 34 mm adjacent to the spigot 30 and decreases to about 12 mm adjacent to the distal spigot 36. Again, these dimensions can be varied in accordance with the size of the airway tube being made. The aforementioned dimensions refer to the uninflated cuff.

Figure 17:
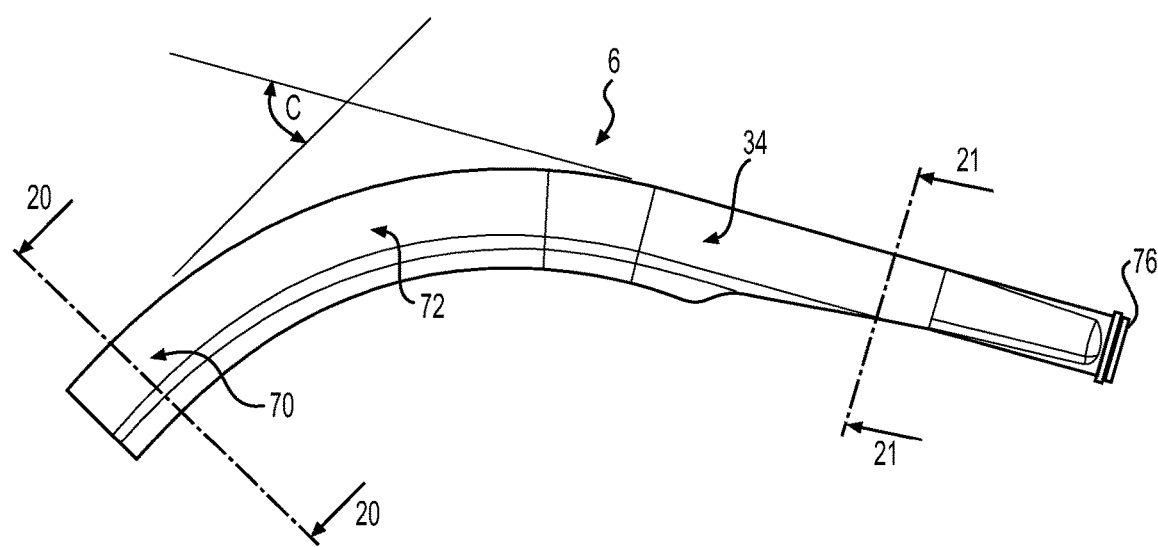
FIG. 17 is a side view of the airway tube.
Figure 18:
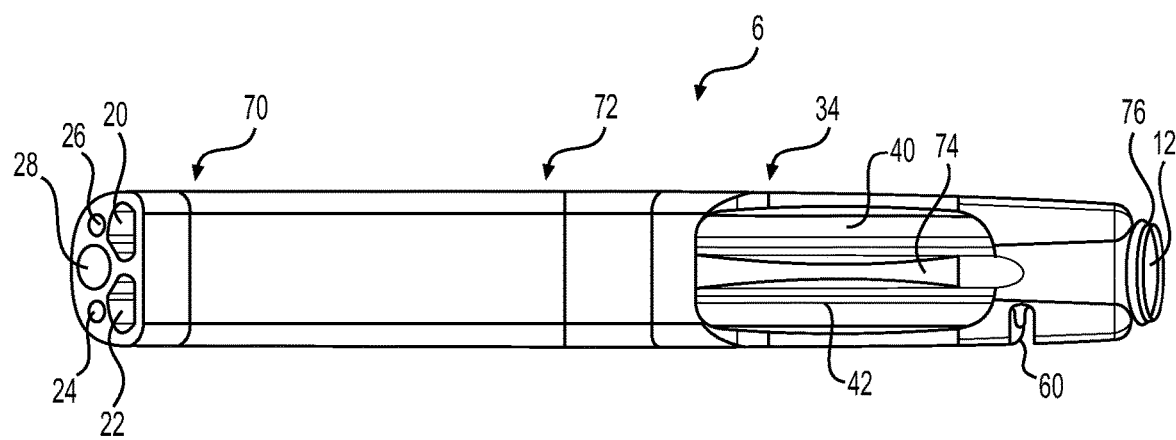
FIG. 18 is a plan view from the anterior side of the airway tube.
Figure 19:
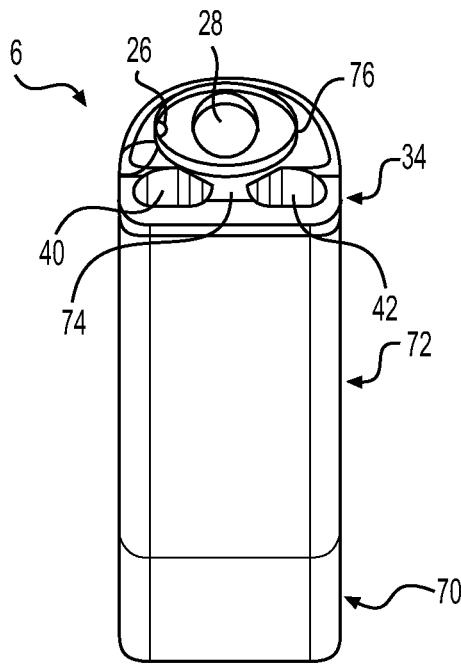
FIG. 19 is an end view of the airway tube.
Figure 20:
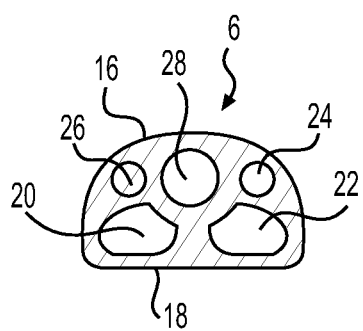
FIG. 20 is a cross-sectional view along the line 20-20.
Figure 21:
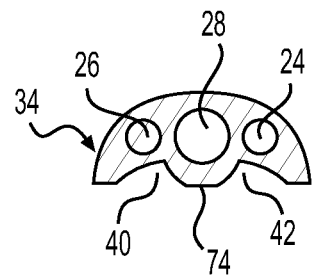
FIG. 21 is a cross-sectional view along the line 21-21.
Figure 22:
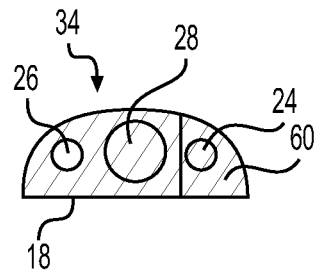
FIG. 22 is a cross-sectional view along the line 22-22.
Figure 23:
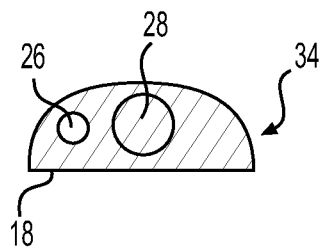
FIG. 23 is a cross-sectional view along the line 23-23.
Figure 24:
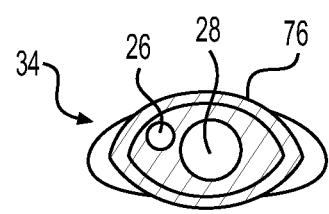
FIG. 24 is a cross-sectional view along the line 24-24.
Figure 25:
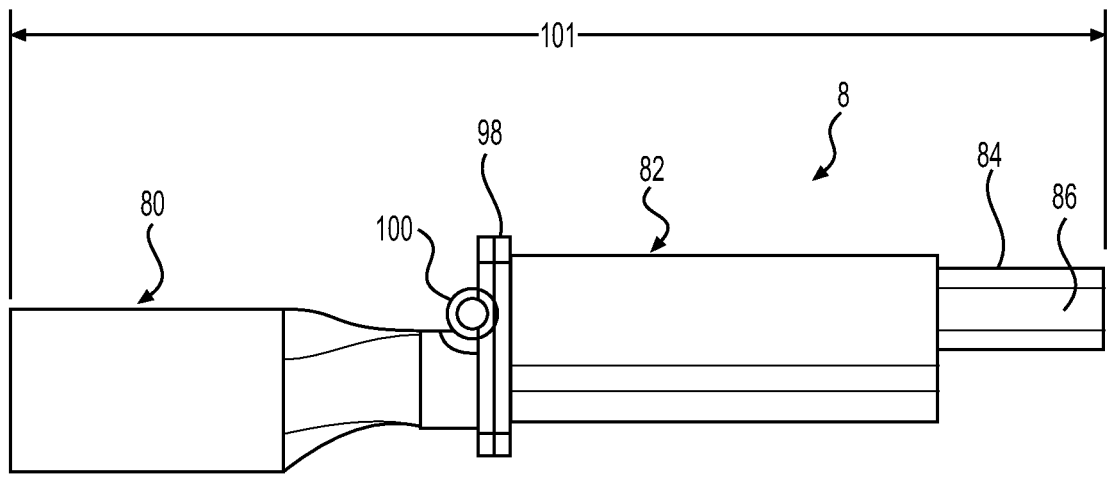
FIG. 25 is a side view of the connecting body.
Figure 27:
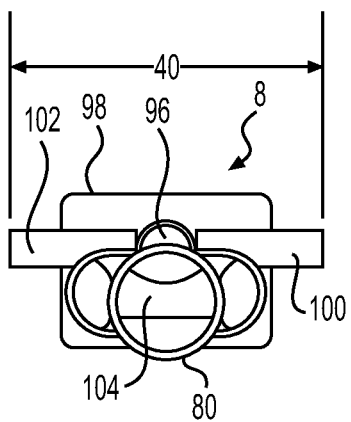
FIG. 27 is a proximal end view of the connecting body.
Figure 28:
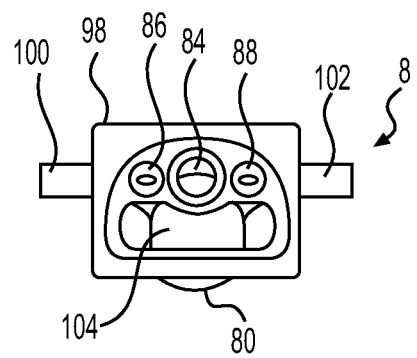
FIG. 28 is a distal end view of the connecting body.

FIGS. 15 to 24 show the preferred shape of the airway tube 6. The airway tube 6 is preferably injection moulded from silicon rubber having a Shore A hardness of 35 and preferably within the range from 35 to 50. It will be seen from FIG. 17 that the end portion 34 forms an angle C with the proximal end portion 70, there being a curved intermediate portion 72 therebetween. Preferably angle C is in the range 50° to 75° and most preferably about 60°. It is preferred that the airway tube 6 is initially injection moulded in a straight condition and then heated in a former so as to form the curved portion 72. The conduits 20, 22, 24, 26 and 28 can all be formed during the moulding process. Similarly, the openings 40 and 42 can also be formed in the moulding process. As best seen in FIG. 18, a central longitudinally-extending ridge 74 is formed between the openings 40 and 42. The ridge 74 imparts additional rigidity to the end portion 34 of the airway tube 6. It further serves to prevent the epiglottis of the patient obstructing the openings 40 and 42. It will also be seen from FIGS. 16 and 17 that the distal end of the end portion 34 tapers somewhat so as to better conform to the interior shape of the cuff 4. The distal end of the end portion 34 is moulded with an integral hollow projection 76 which is of a generally oval shape in cross-section. The outer shape of the projection 76 is generally complementary to the shape of the distal spigot 36 and is located therein so as to impart additional rigidity to the shape of the evacuation chamber 12. It will be seen from FIG. 24 that the distal ends of the conduits 26 and 28 open into the interior of the projection 76 so as to provide fluid communication with the chamber 12. Finally, the notch 60 can also be integrally formed during the moulding process.

It will be appreciated from FIGS. 17 and 18 that the airway tube 18 could be regarded as being generally uniform in cross-section along its length except that the end part 34 has part of the flat anterior side 18 removed. In an area corresponding to the recess 14, the anterior wall 18 is completely removed in a generally rectangular shape but having rounded corners at the distal and proximal ends, as seen in FIG. 18. The edges of the sidewalls 53, 54, 55 and the rim 56 are bonded to the airway tube adjacent to this opening by means of silicone glue. It will be appreciated, however, that from a functional point of view the cuff could be connected to the airway tube in different ways. For instance, parts corresponding to the sidewalls 53, 54, 55 and 57 could be integrally moulded with the airway tube, although this would make moulding of the tube more difficult. If, however, this modification were made the inner edges of the anterior sealing wall 52 could be bonded to the adjacent lower edges of the sidewalls integrally formed with the airway tube. Other intermediate variations would also be possible. It is preferred, however, to mould the airway tube 6 and the cuff 4 as shown in the drawings.

It will be appreciated that the airway tube 6 could be formed in two separate parts. The end part 34 could be moulded separately from the parts 70 and 72 which could be formed by extrusion bent into the correct shape and then joined to the end portion 34.

In one embodiment, the length of the airway tube 6 is about 170 mm (when straight) and the transverse width is about 25 mm. The height, that is to say as measured from the anterior side 18 to the posterior side 16, is about 15 mm. The dimensions of course can be varied according to the size of the airway device which is to be made.

FIGS. 26 to 31 illustrate in more detail the connector body 8. In the illustrated arrangement, the connector body is integrally moulded from plastics material such as polycarbonate. It would be possible to mould the body 8 in a number of parts and connect them together by bonding or heat or ultrasonic welding.

The connector body 8 includes a 15 mm male Luer connector 80 formed at the proximal end of the body. The body includes an intermediate portion 82 from which project three distal spigots 84, 86 and 88. The spigots 84, 86 and 88 have outer diameters such that they can be snugly inserted in the proximal ends of the conduits 28, 26 and 24 respectively so as to establish fluid communication with these conduits. The spigots may be slightly tapered to facilitate assembly of the connector body 8 onto the airway tube 6. The lengths of the spigots are about 15 mm.

Figure 26:
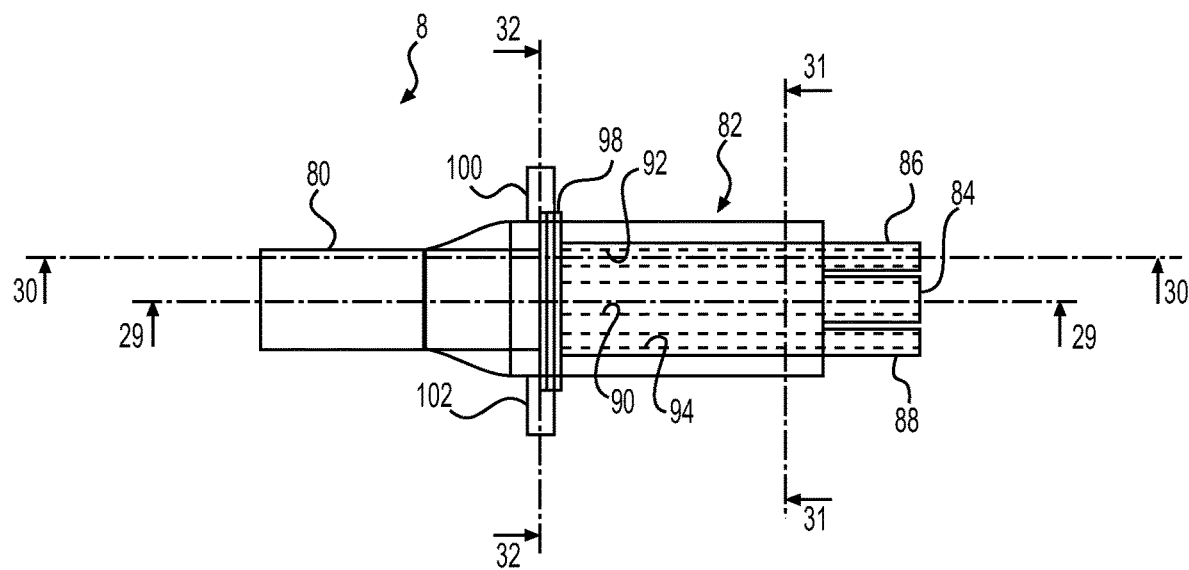
FIG. 26 is a plan view from the anterior side of the connecting body.
Figure 29:
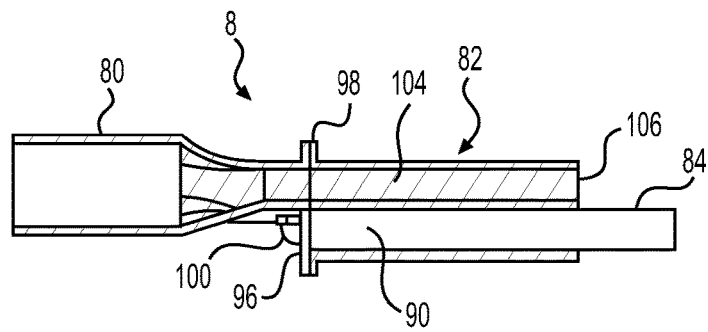
FIG. 29 is a longitudinal cross-sectional view along the line 29-29.
Figure 30:
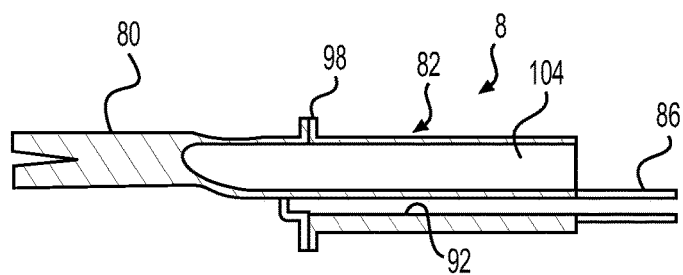
FIG. 30 is a longitudinal cross-sectional view along the line 30-30.

As can be best seen from FIG. 26 the intermediate portion 82 includes passages 90, 92 and 94 which communicate with the hollow spigots 84, 86 and 88 respectively. The proximal end of the passage 90 is constituted by a port 96 which is formed in a transverse wall 98 and is open to atmosphere. In use air is admitted through the port 96 so that it can pass into the passage 90 and then through the evacuation chamber vent conduit 28 and be admitted to the evacuation chamber 12. The intermediate portion 82 is formed with a laterally-projecting hollow spigot 100 which communicates with the passage 92. The passage 92 is in fluid communication with the hollow spigot 86 which in turn establishes fluid communication with the evacuation conduit 26. In use, a source of suction can be applied via the spigot 100 so as to establish suction within the evacuation chamber 12 to which the distal end of the conduit 26 opens. The intermediate portion 82 is also formed with a laterally-projecting hollow spigot 102 which communicates with the passage 94 which is in fluid communication with the hollow spigot 88. The hollow spigot 88 is inserted into the inflation conduit 24. In use positive pressure can be applied to the spigot 102 via a syringe in order to pressurise the inflation conduit and thus inflate the cuff 4 to the required degree.

The anterior side of the intermediate portion 82 is essentially hollow and forms a relatively wide passage 104 which, at the proximal end is in communication with the Luer connector 80 and at the distal end communicates with the ends of the airway conduits 20 and 22. The distal end of the intermediate portion 82 is formed as a shoulder 106 which abuts the adjacent end of the airway tube 6 so that the passage 104 communicates with the conduits 20 and 22. In the illustrated arrangement, the should 106 abutting the end of the tube 6 is preferred because, if connecting spigots were used to establish fluid communications with the airway conduits 20 and 22, there would be undesirable constrictions caused by the spigots. In other words the direct abutment of the shoulder 106 provides the least amount of obstruction to flow of anaesthetic gases. There is little prospect of leakage between the passage 104 and the other passages at the junction because of the insertion of the spigots 84, 86 and 88 into the corresponding conduits essentially isolates them from the passage 104.

In the illustrated arrangement, the overall length of the connecting body 8 is about 101 mm and the maximum width, that is to say as measured between the ends of the spigots 100 and 102, is 40 mm. It will be appreciated that the rigid body 8 mounted on the proximal end of the airway tube 6 provides rigidity at this point of the artificial airway which is sometimes useful for fixing of the position of the artificial airway. This also prevents the airway being damaged or obstructed in the event of the patient biting upon the airway. Furthermore, the connecting sleeve 10 provides a soft resilient surface that will prevent damage to the patients teeth should biting occur.

Figure 31:
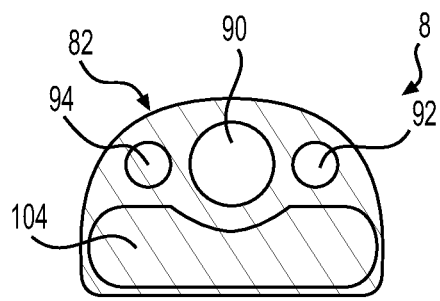
FIG. 31 is a transverse cross-sectional view along the line 31-31.
Figure 32:
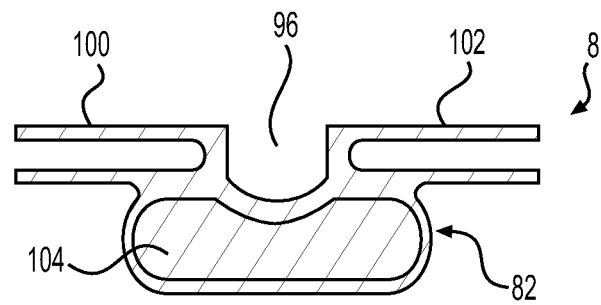
FIG. 32 is a transverse cross-sectional view along the line 32-32.

The cross-section shape of the periphery of the intermediate portion as shown in FIG. 31 corresponds to the cross-sectional shape at the proximal end of the airway tube 6. This enables the connecting sleeve 10 to be snugly mounted over the intermediate portion 82 and the proximal end of the tube 6.

Figure 33:
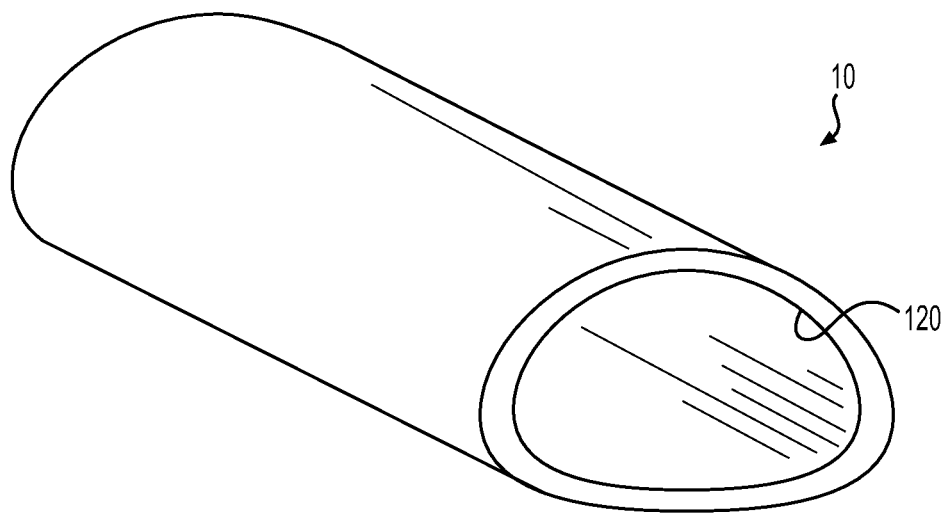
FIG. 33 is an isometric view of a sealing sleeve.
Figure 34:
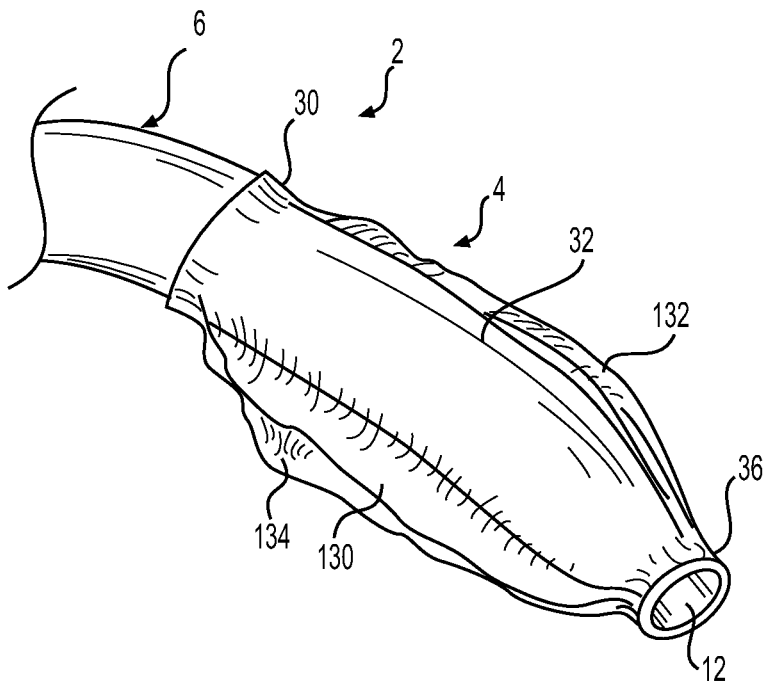
FIG. 34 is a schematic view of the posterior side of the cuff in a deflated state.
Figure 35:
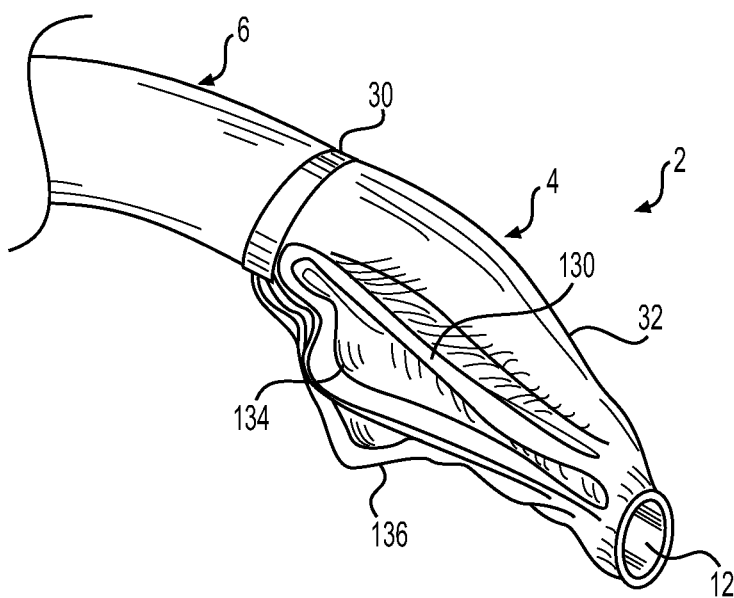
FIG. 35 is a schematic view of the anterior side of the cuff in a deflated state.
Figure 36:
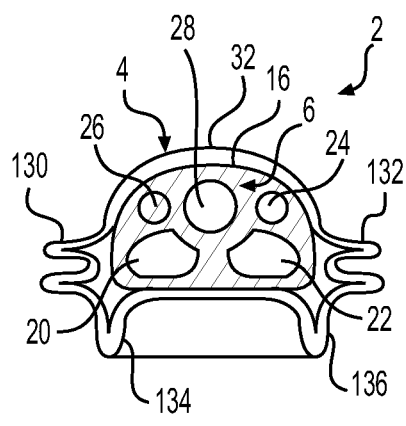
FIGS. 36 to 39 are schematic cross-sectional views of the deflated cuff corresponding to FIGS. 6 to 9 respectively.
Figure 37:
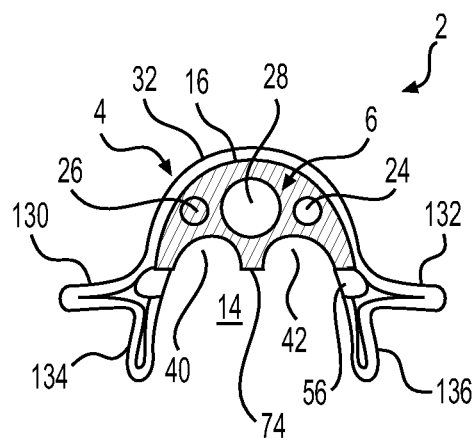
Figure 38:
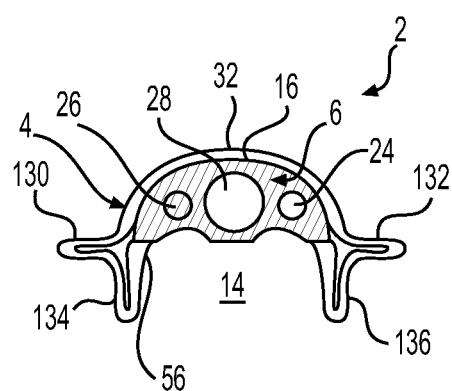
Figure 39:
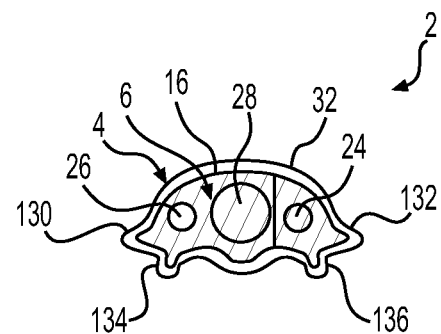
Figure 40:
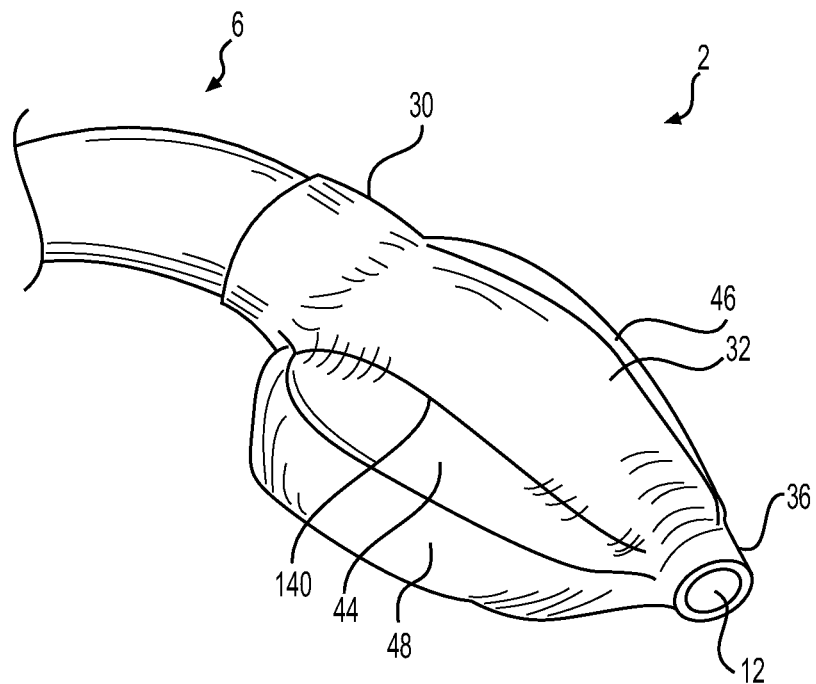
FIG. 40 is a schematic view of the posterior side of the cuff in an inflated state.
Figure 41:
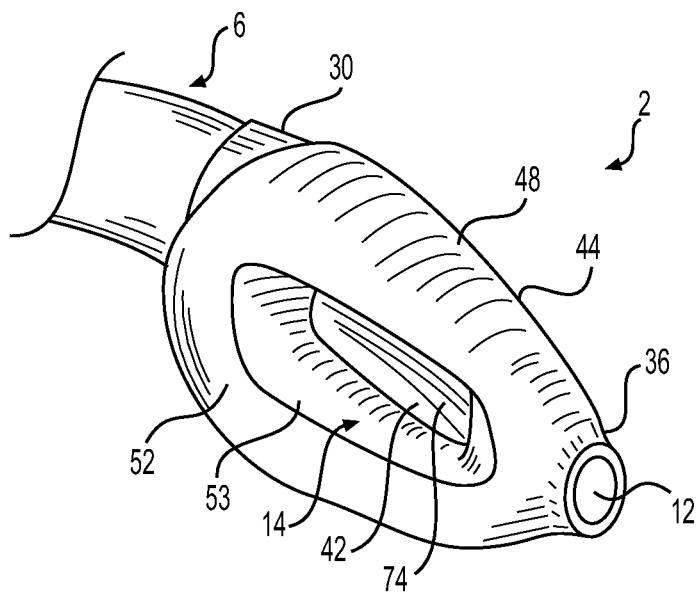
FIG. 41 is a schematic view of the anterior side of the duff in an inflated state.
Figure 42:
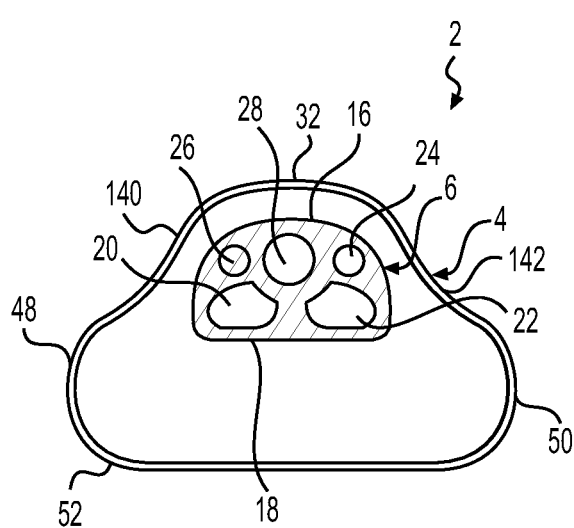
FIGS. 42 to 45 are schematic cross-sectional views of the inflated cuff corresponding to the cross-sectional views of FIGS. 6 to 9 respectively.

FIG. 33 shows the sleeve 10. It is extruded or moulded from silicon rubber and has a hardness which is similar to that of the airway tube 6. The tube 10 has a bore 120 which is of complementary shape to the outer surface of the intermediate portion 82 and the airway tube 6. The length of the sleeve 10 is preferably about 60 mm. From a functional point of view it needs to be longer than the length of the intermediate portion 82 as measured from the wall 98 to the shoulder 106 so that the sleeve 10 fully covers the exterior of the intermediate portion 82 and about 20 mm of the proximal end of the airway tube 6.

The preferred sequence of fabrication of the device is to separately mould the cuff 4, airway tube 6, connector body 8 and sleeve 10. The initially straight airway tube 6 is then heat formed into a curved shape as described previously. The cuff 4 can then be mounted on the end portion 34 of the airway tube 6 and bonded thereto as described earlier. The sleeve 10 can then be slid along the proximal end of the airway tube 6 so that the spigots 84, 86 and 88 can be inserted into their respective conduits. Silicon bonding agent may also be used to fix them in position. Silicon bonding agent is then applied to the bore 120 of the sleeve and it is moved in a proximal direction so that is proximal end engages the transverse wall 98. In this way a gas tight join is formed between the connector body 8 and the end of the airway tube 6 with the necessary fluid communication paths established.

FIGS. 34 to 39 schematically illustrate the cuff in its fully deflated position. The cuff can be deflated by connecting a syringe to a lumen (not shown in FIGS. 34 to 39) connected to the spigot 102. The cuff 4 is deflated so that it can be more easily inserted through the mouth and throat of the patient. It will be seen that, when the cuff is deflated, the lobes 44 and 46 collapse so as to form laterally-extending wings 130 and 132 which vary in size and shape towards the distal ends of the cuff. The anterior surface 52 and the inner sidewalls 54 collapse so as to form anteriorly-extending wings 134 and 136 which again vary in shape and width along the length of the cuff. The wings 130, 132, 134 and 136 are somewhat randomly oriented but more importantly they can readily be resiliently deflected during the insertion process.

Figure 43:
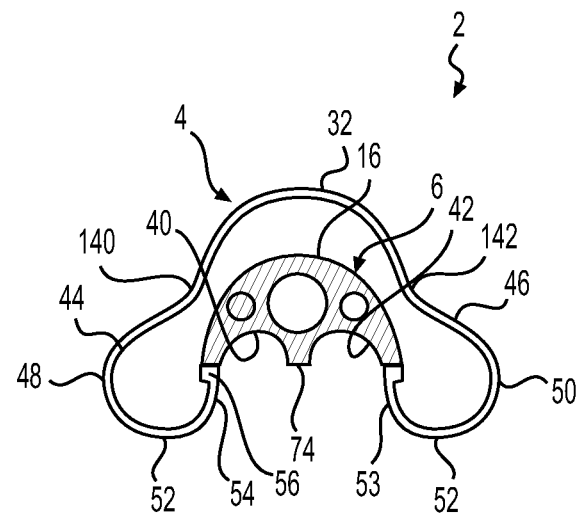
Figure 44:
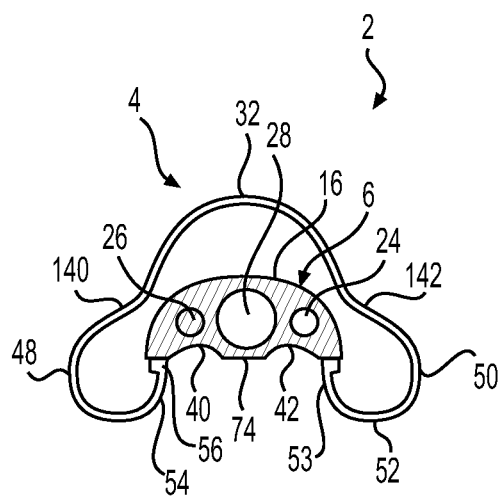
Figure 45:
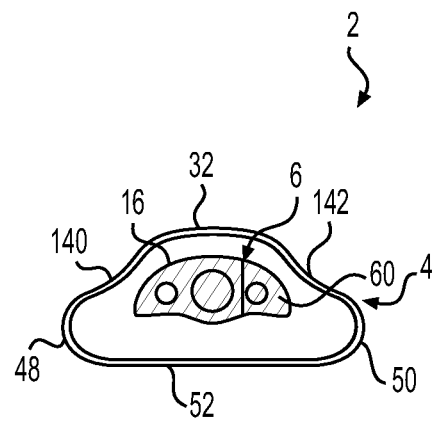

FIGS. 40 to 45 schematically show the shape of the cuff, in its inflated position. Normally the cuff 4 is inflated to a pressure within the range 40-60 cm $H_2O$ pressure. In the inflated position, the lobes 44 and 46 are somewhat extended laterally. More significantly however the posterior wall 31 is significantly displaced from the posterior wall 16 of the end portion 34 of the airway tube 6, as best seen in FIG. 43. In the inflated position, there are still longitudinal depressions 140 and 142 generally located between the lobes 44 and 46 and the adjacent parts of the posterior wall 31, as seen in FIG. 43. The depressions 140 and 142 serve to impart some stability to the inflated structure to intend to resist twisting thereof, after or during inflation.

After inflation, the maximum width of the cuff 4 is about 52 mm and the maximum height as measured between the anterior sealing surface 52 and the posterior wall 31 is about 33 mm for a size 4 device and these dimensions will vary with smaller and larger devices as is well known in the art.

Figure 46:
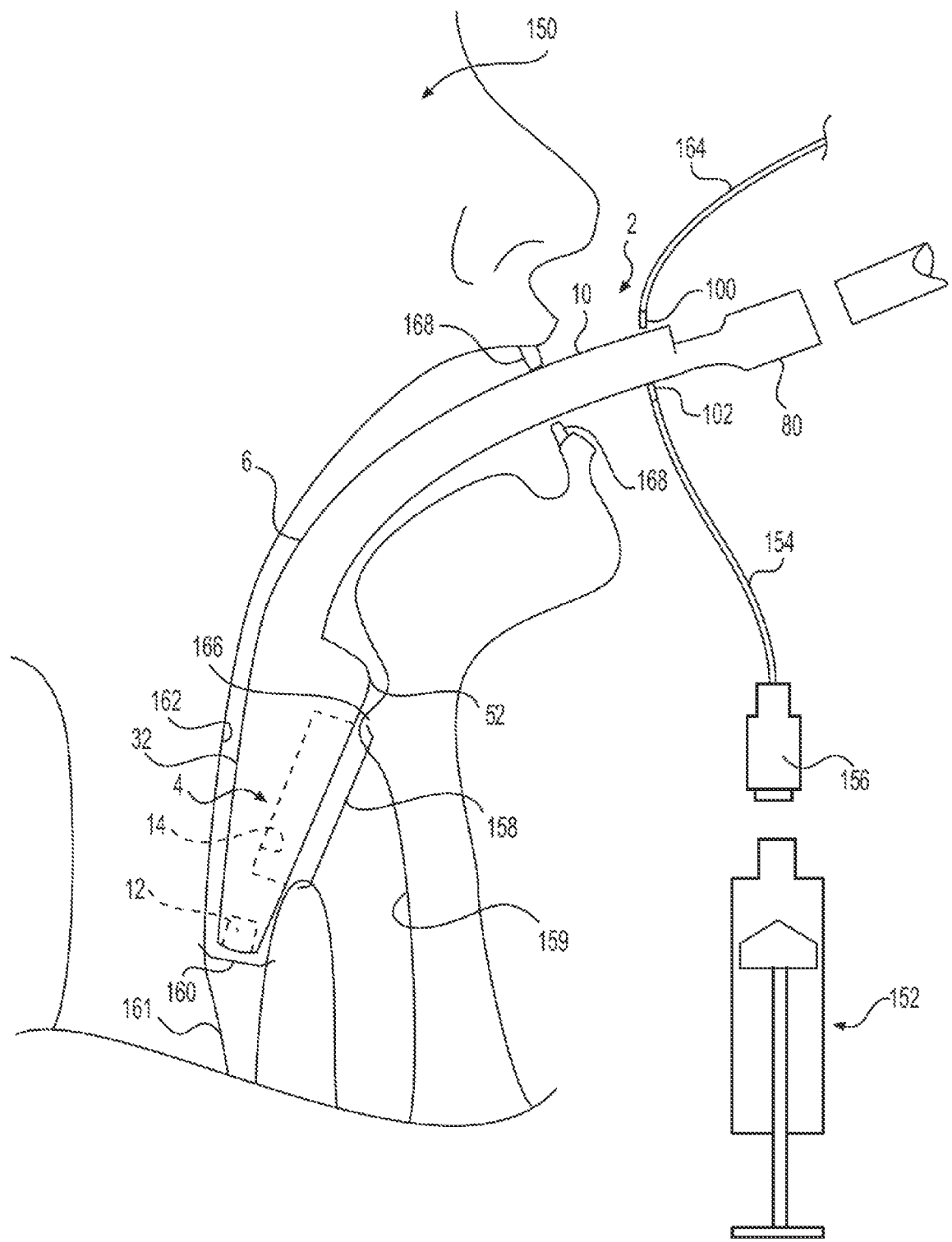
FIG. 46 is a schematic view showing deployment of the artificial airway in a patient.

FIG. 46 diagrammatically illustrates the manner in which the artificial airway 2 is deployed in a patient 150. The cuff 4 is initially deflated by using a syringe 152 which is connected to the spigot 102 by means of a lumen 154 via a valve 156 which normally closes the lumen 154 except when the syringe 152 is connected thereto. The artificial airway 2 can then be inserted through the throat of the patient until the cuff is located adjacent to the glottic opening 158. The distal end of the cuff 4 is located adjacent to the upper oesophageal sphincter 160. The syringe 152 can then be used to inflate the cuff 4 to the required degree. This causes outward expansion of the posterior wall 31 of the cuff so as to seal against the posterior pharyngeal walls 162 of the patient. Inflation of the cuff also causes some lateral expansion of the sidewalls 48 and 50 so that these seal against the lateral pharyngeal walls of the patient. During this process, the anterior wall 52 will be brought into good sealing contact with the area surrounding the glottic opening 158. Anaesthetic gases or air as required can then be administered to the patient via the Luer connector 80.

The shape of the cuff as described above generally anatomically conforms to the corresponding anatomical features of the patient whereby an excellent seal is maintained between the anterior wall 52 and the area surrounding the glottic opening 158. A prototype of the device has been tested and it has been found that the seal is higher than is available with currently available airway devices. The prototype of the invention has been tested at a pressure of 28 to 36 cm of $H_2O$ whereas most currently available commercial airways typically have a maximum of about 28 cm $H_2O$.

Also it will be seen that the evacuation chamber 12 is presented to the oesophagus 161 of the patient. A source of suction can be connected via a lumen 164 to the spigot 100 in order to cause suction within the chamber 12. Because however the chamber 12 is vented to atmosphere by the evacuation chamber vent conduit 28, there is only a limited amount of suction towards the proximal part of the chamber 12. This avoids the undesirable effect of having the chamber 12 sucked directly onto the tissue surfaces of the patient which could cause damage. Any material regurgitated from the oesophagus 161 will enter the chamber 12 and will be entrained into the flow of air which passes from the evacuation chamber vent conduit 28 into the evacuation conduit 26. This minimises the possibility that the regurgitated material would enter the glottic opening and into trachea 159. The chamber 120 is vented to atmosphere, there is very little prospect that the chamber could be maintained in a state of suction against the mucosa of the upper oesophageal sphincter or parts adjacent thereto. This avoids the possibility of damage to the tissue of the patient. Also the arrangement has advantages over prior art arrangements in which evacuation tubes can communicate directly with the oesophagus of the patient and apply negative pressure thereto which could have the effect of inducing regurgitation.

It will also be observed that the epiglottis 166 of the patient is normally located adjacent to the recess 14 and the ridge 74 of the airway tube tends to prevent the epiglottis obstructing the airways openings 40 and 42. Also it will be seen from FIG. 46 that the teeth 168 of the patient are located adjacent to the sleeve 10 which is resilient as it is formed from silicon rubber. This helps to prevent damage to the patient and to the artificial airway.

FIGS. 47 to 64 show details of a modified airway constructed in accordance with the invention. In these drawings, the same reference numerals have been used to denote parts which are the same as or correspond to those of the first embodiment.

Figure 64:
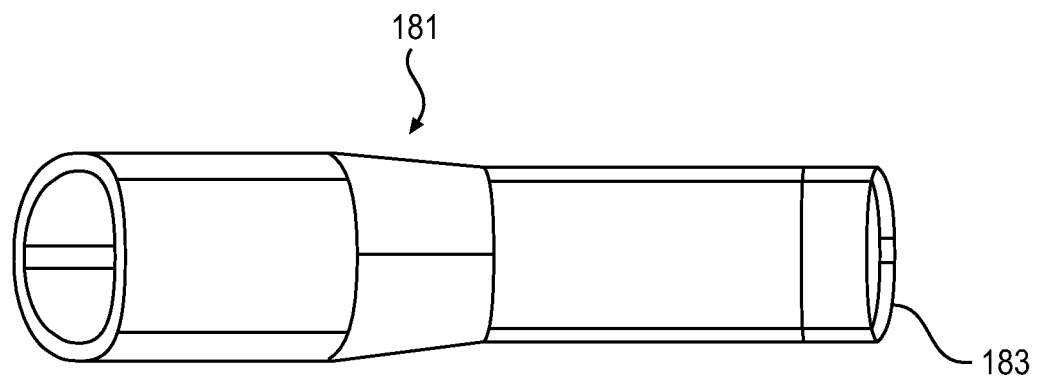
FIG. 64 is a plan view showing the anterior side of the second component.

In this embodiment, the airway tube 6 is made in two components, a distal component 180 which is interconnected with a proximal component 181. These components are joined together by means of bonding or gluing or the like and when connected together correspond in shape to the airway 6. The proximal component 181 can be connected to the joining sleeve 10 as in the previous embodiment. The distal component 180 includes a rebate 182 which, in use, connects to a complementary rebate 183 formed in the distal end of the proximal component 181, as best shown in FIG. 64. The rebates 182 and 183 facilitate alignment and gluing or bonding thereto. The component 180 includes a projecting wall 184 which projects somewhat from the anterior side of the component 180. The interior of the wall 184 defines an elongate oval shaped recess 186 which corresponds to the recess 14 of the cuff.

Figure 47:
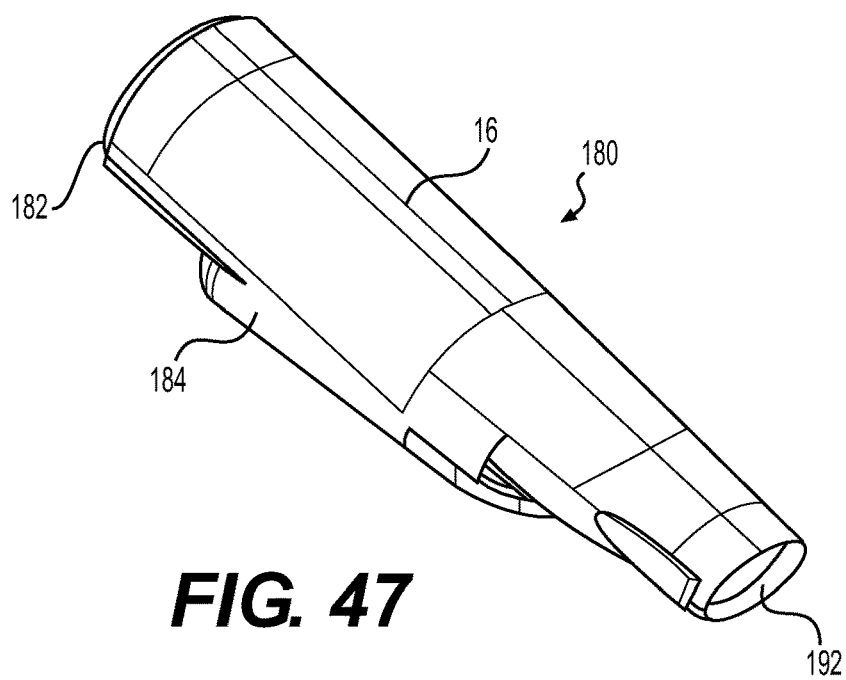
FIG. 47 is an isometric view of a distal end component of an airway tube of a second embodiment of the invention.
Figure 48:
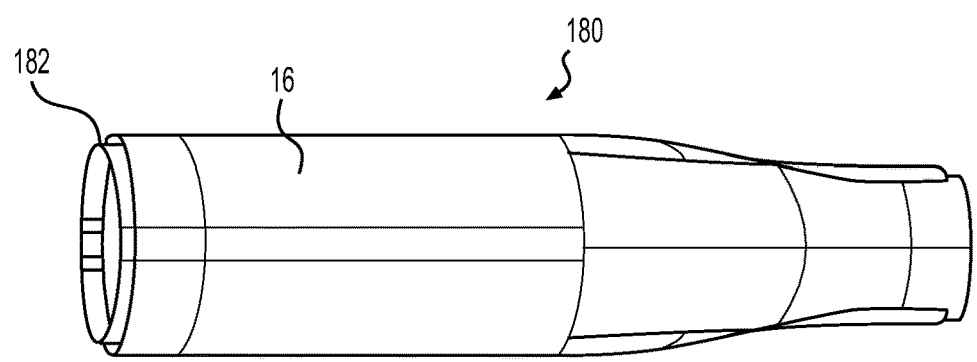
FIG. 48 is a view showing the posterior side of the component shown in FIG. 47.
Figure 49:
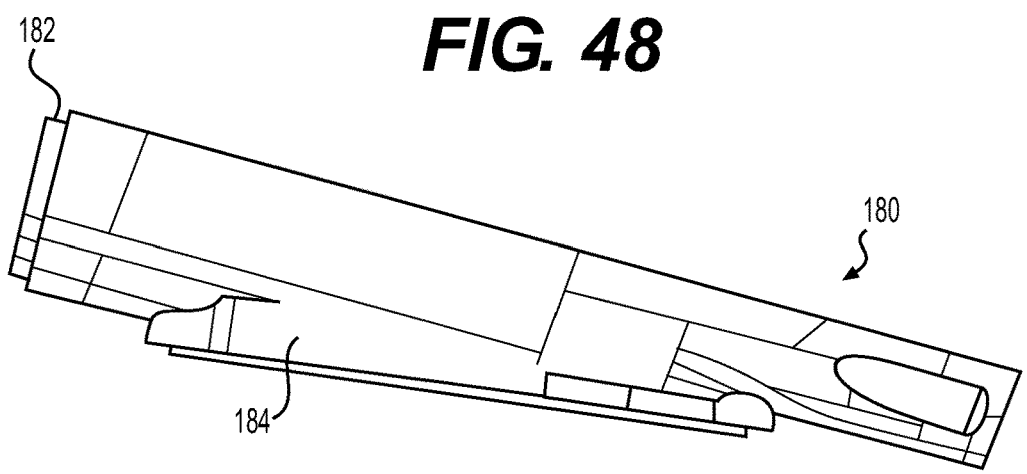
FIG. 49 is a side view of the component of FIG. 47.
Figure 50:
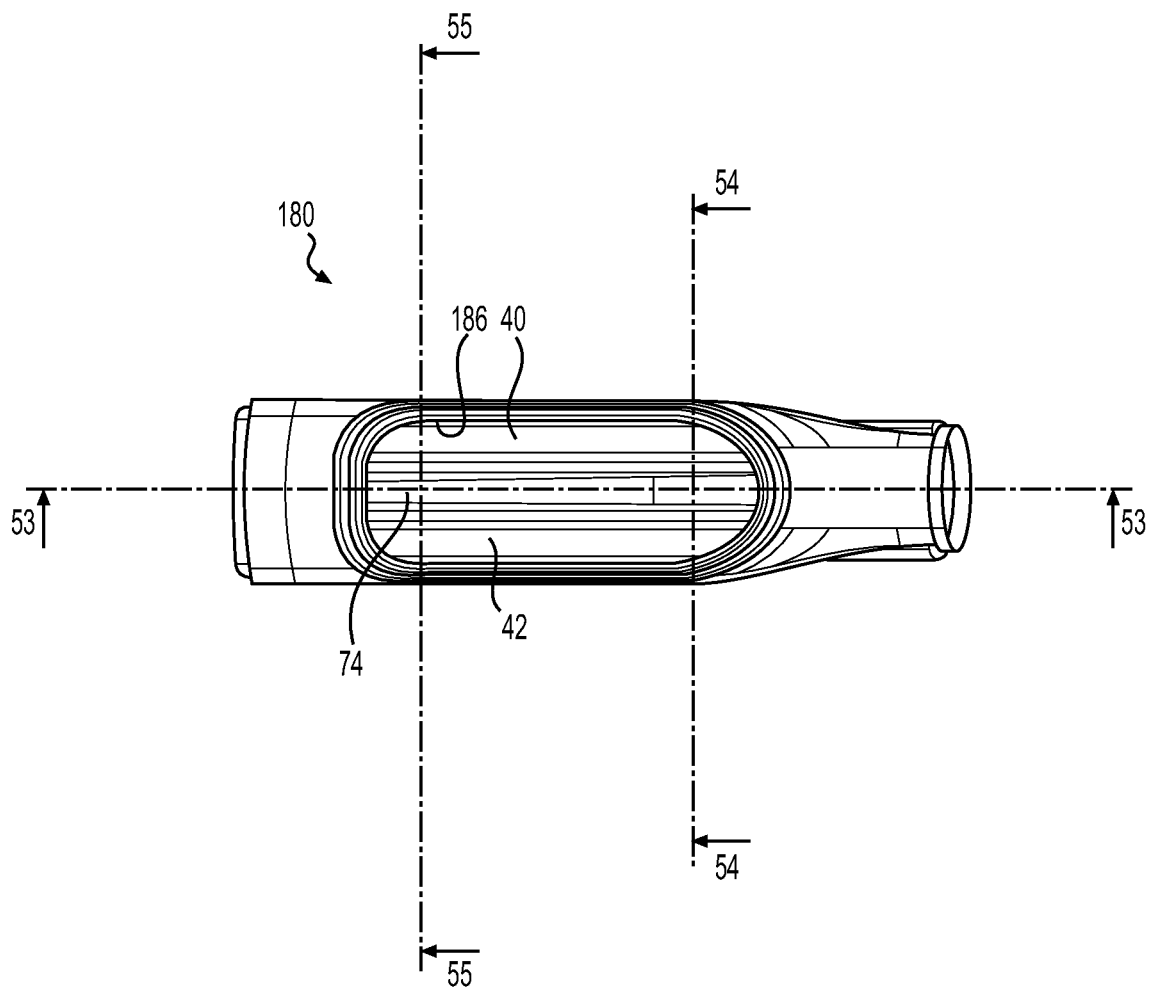
FIG. 50 is a plan view showing the anterior side of the component of FIG. 47.
Figure 51:
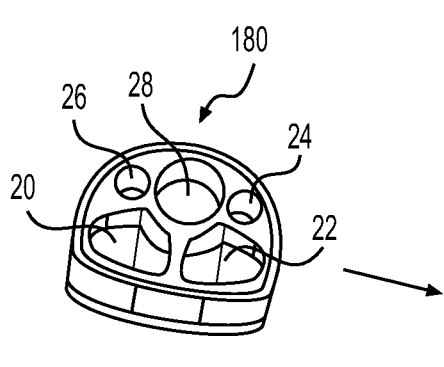
FIG. 51 is a view into the proximal end of the component.
Figure 52:
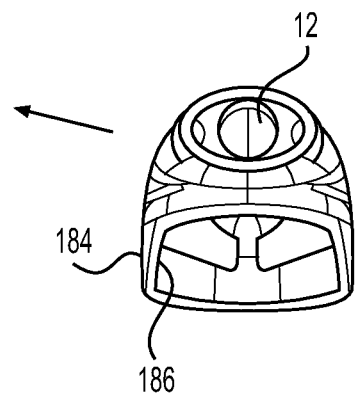
FIG. 52 is a view into the distal end of the component.
Figure 57:
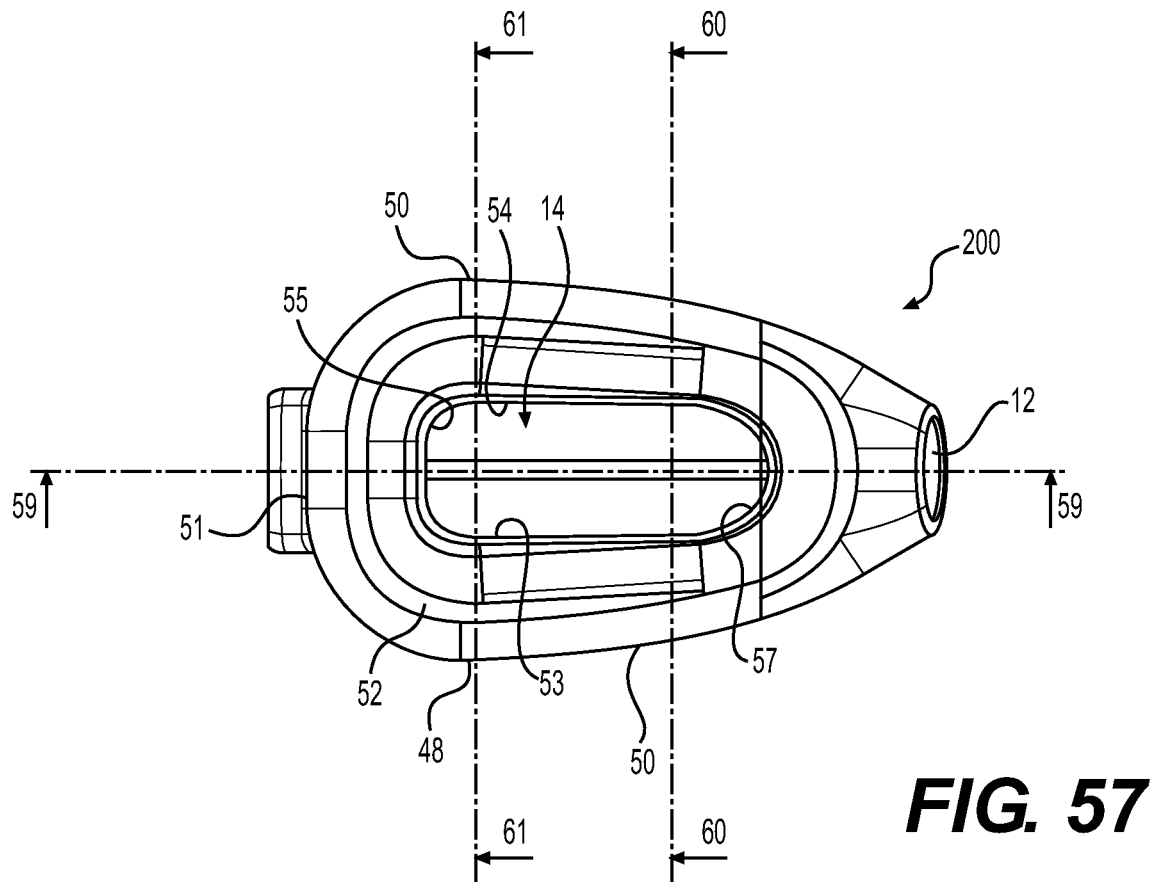
FIG. 57 is a plan view showing the anterior side of the cuff of FIG. 56.

As best seen in FIGS. 53, 54 and 55, the anterior edge of the wall 184 is formed with a groove 188 and shoulder 190 outwardly adjacent thereto. The component 180 includes a rebate 192 surrounding the vent conduit 28 at its distal end, as best seen in FIGS. 47 and 53.

By forming the airway tube in proximal and distal components 181 and 180 they are each easier to mould than a single component and this therefore reduces the overall cost of the device.

FIGS. 57 to 61 illustrate a modified form of cuff 200 which is shaped so as to facilitate mounting onto the component 180. The cuff 200 differs in two significant ways from that shown in the previous embodiment.

The first difference is that the inner sidewalls 53, 54, 55 and 57 are formed with a lip 202 which projects generally inwardly relative to the recess 14. The lip 202 is shaped so as to be received within the groove 188 of the component 180 and adjacent to the shoulder 190. This facilitates bonding and or gluing of the cuff to the component 180. This is best seen in the enlarged schematic view of FIG. 62.

Figure 59:
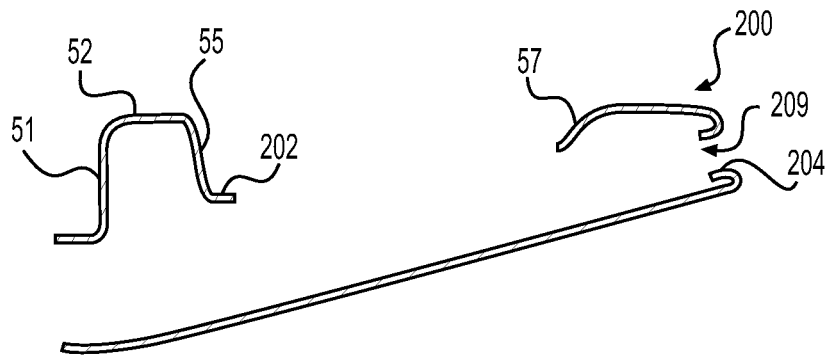
FIG. 59 is a schematic cross-sectional view along the line 59-59.
Figure 58:
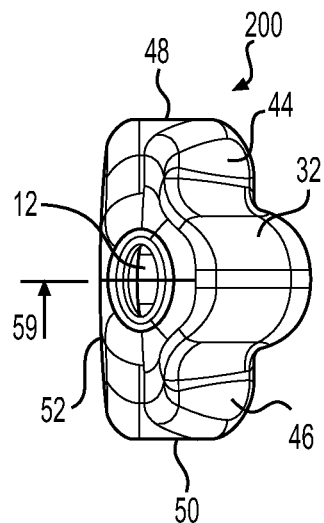
FIG. 58 is a distal end view of the cuff of FIG. 56.
Figure 60:
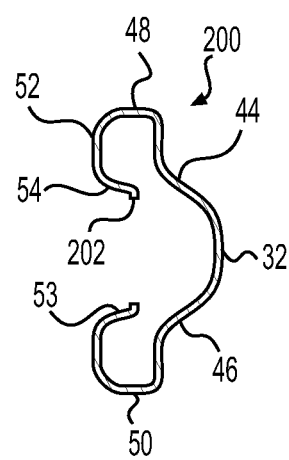
FIG. 60 is a schematic cross-sectional view along the line 60-60.
Figure 61:
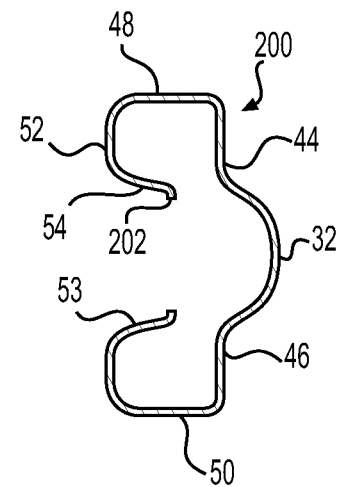
FIG. 61 is a schematic cross-sectional view along the line 61-61.
Figure 62:
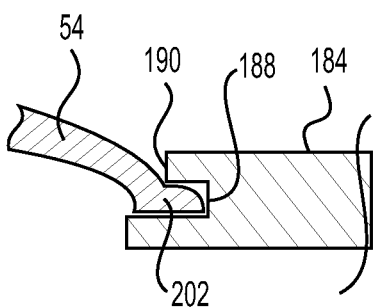
FIG. 62 is an enlarged fragmentary view showing interconnection of the distal end component with the modified form of cuff.
Figure 63:
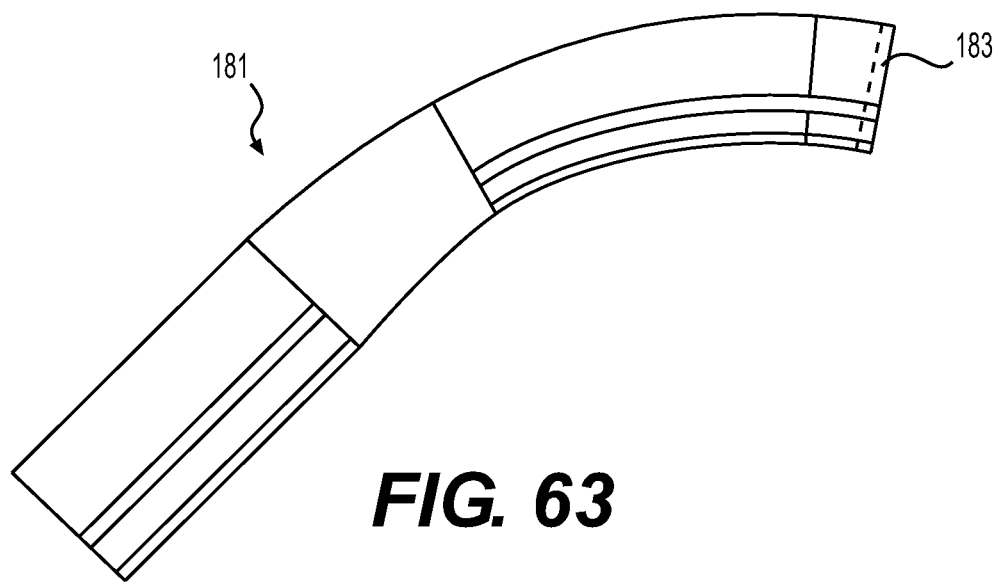
FIG. 63 is a side view of a second component of the airway tube.

The second major change that the cuff 200 has relative to the cuff 4 of the previous embodiment is that the distal spigot 36 is formed with an inwardly directed integral flange 204, as best shown in FIG. 59. The flange 204 is, in use, located within the rebate 192 formed at the distal end of the component 180. The provision of the flange 204 therefore defines a smooth entrance to the evacuation chamber 12. Further, any excess glue or bonding agent, if present, will be located inwardly of the proximal end of the airway so that there should not be any rough or sharp edges at the distal end caused by such excess glue or bonding agent. The appearance of the cuff is also enhanced because it has a smooth entrance to the evacuation chamber 12.

In the cuff which is formed with the component 180 and cuff 200, the proximal connecting spigot 30 of the cuff is sufficiently long that it covers the join line between the component 180 and the remainder of the airway tube. This helps to prevent any gas leakages and also gives a neat appearance to the airway. Further, any excess glue or bonding agent used to interconnect the component 180 with the remainder of the airway would be covered by the spigot 30 and therefore avoid any unwanted projections on the exterior of the airway caused by such excess glue or bonding agent.

It will be appreciated by those skilled in the art that the device of the invention is moulded from relatively few components which are inexpensive to make. Further, the assembly process is comparatively simple compared with the assembly needed for known artificial airways.

It will also be appreciated by those skilled in the art that the shape of the cuff of the invention is wedge shaped, as described above, when viewed in side view and plan. This provides better conformity with the anatomical shape of a patient when the cuff is inflated compared with the elliptical or oval toroidal or annular rings of most prior art devices.

The device of invention is thus inexpensive enough that it can be made as a single use or disposable device but it could be auto-clavable for multiple use.

The described construction has been advanced merely by way of example and many modifications and variations may be made without departing from the spirit and scope of the invention, which includes every novel feature and combination of features herein disclosed.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge.

LIST OF PARTS artificial airway 2
an inflatable cuff 4
airway tube 6
connector body 8 joining sleeve 10
evacuation chamber 12
recess 14
curved posterior side 16
generally flat anterior side 18
airway conduits 20, 22
inflation conduit 24
evacuation conduit 26
evacuation chamber vent conduit 28
proximal connecting spigot 30
posterior wall 31
semi-cylindrical portion 32
distal end portion 34
distal spigot 36
airway openings 40, 42
extending lobes 44, 46
lateral sidewalls 48, 50
proximal end wall 51
anterior sealing wall 52
inner sidewalls 53, 54
proximal inner sidewall 55
rim 56
distal inner sidewall 57
rebate 58
notch 60
proximal end portion 70
curved intermediate portion 72
central longitudinally-extending ridge 74
integral hollow projection 76
male Luer connector 80
intermediate portion 82
distal spigots 84, 86, 88
passages 90, 92, 94
port 96
transverse wall 98
laterally-projecting hollow spigot 100
laterally-projecting hollow spigot 102
relatively wide passage 104
shoulder 106
bore 120
laterally-extending wings 130, 132
anteriorly-extending wings 134, 136
longitudinal depressions 140, 142
patient 150
syringe 152
lumen 154
valve 156
glottic opening 158
trachea 159
upper oesophageal sphincter 160
oesophagus 161
pharyngeal walls 162
lumen 164
epiglottis 166
teeth 168
distal component 180
proximal component 181
rebate 182, 183
projecting wall 184
recess 186
groove 188
shoulder 190
rebate 192
cuff 200
lip 202
flange 204

What is claimed is:

1. An artificial airway including:
an airway tube including at least one airway conduit;
an inflatable cuff mounted on a distal end of the airway tube;
a support member extending into the inflatable cuff, the inflatable cuff having inner side walls, anterior walls and a posterior wall, the inner side walls being joined to the support member to define a recess which communicates with the at least one airway conduit, the anterior walls and the posterior wall, sealingly engaging, in use, about the glottic opening and the posterior pharyngeal wall respectively of a patient;
an evacuation chamber located at a distal end of the inflatable cuff, the evacuation chamber, in use, being in fluid communication with the oesophagus of a patient;
an evacuation conduit in fluid communication with the evacuation chamber; and
a ventilation conduit in fluid communication with the evacuation chamber, the arrangement being such that, in use, suction is applied to the evacuation conduit whereby regurgitated material entering the evacuation chamber is removed through the evacuation conduit and wherein the ventilation conduit substantially prevents a negative pressure being applied to the tissue of the patient.

2. An artificial airway as claimed in claim 1, wherein the support member defines a posterior wall of the recess.

3. An artificial airway as defined in claim 1, wherein the support member is integral with the airway tube.

4. An artificial airway as claimed in claim 1, wherein the airway tube is formed by a proximal part and a distal part which are separately formed then joined together.

5. An artificial airway as claimed in claim 4, wherein the distal part is integrally formed with said support member.

6. An artificial airway as claimed in claim 5, wherein the support member is molded with an opening which includes first formations and the inner side walls of the inflatable cuff are molded with second formations which are complementary to the first formations, the first and second formations being interconnectable to facilitate joining of the inflatable cuff to the support member.

7. An artificial airway as claimed in claim 6, wherein the inflatable cuff includes a proximal and distal spigots which overlie adjacent parts of the airway tube and wherein the inflatable cuff is only joined to the airway tube adjacent to said proximal and distal spigots and by said first and second formations.

8. An artificial airway as claimed in claim 7, wherein the airway tube includes the evacuation conduit which communicates with the evacuation chamber located at the distal end of the inflatable cuff.

9. An artificial airway as claimed in claim wherein the distal spigot includes an integral posteriorly directed flange which lies within a distal part of the evacuation conduit so that an entrance to the evacuation chamber is defined by the material of the inflatable cuff.

10. An artificial airway including:
an airway tube having at least one airway conduit therein;
a cuff mounted on a distal end of the airway tube and having a recess which is in fluid communication with the at least one airway conduit;
an evacuation chamber located at a distal end of the cuff, the chamber, in use, being in fluid communication with the oesophagus of a patient;
an evacuation conduit in fluid communication with the evacuation chamber; and a ventilation conduit in fluid communication with the evacuation chamber, the arrangement being such that, in use, suction is applied to the evacuation conduit whereby regurgitated material entering the evacuation chamber is removed through the evacuation conduit and wherein the ventilation conduit substantially prevents a negative pressure being applied to the tissue of the patient.

11. An artificial airway as claimed in claim 10, wherein the ventilation conduit vents the evacuation chamber to atmosphere.

12. An artificial airway comprising:
an airway tube having at least one airway conduit therein;
an inflatable cuff mounted on a distal end of the airway tube, an end portion of the airway tube extending into the inflatable cuff, the inflatable cuff including a recess which is defined by the end portion of the airway tube and inner sidewalls of the inflatable cuff which are sealingly connected to said end portion and wherein said at least one airway conduit is in fluid communication with said recess;
the inflatable cuff including an anterior sealing wall which merges from the inner sidewalls, the anterior sealing wall lying generally in a plane and, in use, sealingly engages the glottic opening of a patient; the inflatable cuff further including a posterior wall extending from outer peripheral parts of the anterior sealing wall to extend over said end portion and, in use, being resiliently extended, on inflation of the inflatable cuff, to sealingly engage the posterior pharyngeal wall of the patient;
a connector body for providing fluid communication with said at least one airway conduit; and
means for sealingly connecting the connector body to the proximal end of the airway tube.

13. An artificial airway including:
an airway tube having at least one airway conduit therein;
an inflatable cuff mounted on a distal end of the airway tube, an end portion of the airway tube extending into the inflatable cuff, the inflatable cuff including a recess which is defined by the end portion of the airway tube and inner sidewalls of the inflatable cuff which are sealingly connected to said end portion and wherein said at least one airway conduit is in fluid communication with said recess;
the inflatable cuff including an anterior sealing wall which merges from the inner sidewalls, the anterior sealing wall lying generally in a plane and, in use, sealingly engages the glottic opening of a patient; the inflatable cuff further including a posterior wall extending from outer
peripheral parts of the anterior sealing wall to extend over said end portion and, in use, being resiliently extended, on inflation of the inflatable cuff, to sealingly engage the posterior pharyngeal wall of the patient;
an evacuation chamber located at a distal end of the inflatable cuff, the chamber, in use, being located adjacent to the upper oesophageal sphincter of a patient;
an evacuation conduit in fluid communication with the evacuation chamber;
and
an evacuation chamber vent conduit in fluid communication with the evacuation chamber;
and wherein at least the evacuation conduit and the evacuation chamber vent conduit are located within said distal end of the airway tube.

14. An artificial airway as claimed in claim 1 wherein said distal end of the airway tube provides structural rigidity for the distal end of the artificial airway.

15. An artificial airway as claimed in claim 14, wherein that the airway does not include a back plate connected to the inflatable cuff or an inflatable ring.

16. An artificial airway including:
an airway tube having at least one airway conduit therein; and
an inflatable cuff mounted on a distal end of the airway tube, an end portion of the airway tube extending into the inflatable cuff, the inflatable cuff including a recess which is defined by the end portion of the airway tube and inner sidewalls of the inflatable cuff which are sealingly connected to said end portion and wherein said at least one airway conduit is in fluid communication with said recess;
the inflatable cuff including an anterior sealing wall which merges from the inner sidewalls, the anterior sealing wall lying generally in a plane and, in use, sealingly engages the glottic opening of a patient; the inflatable cuff further including a posterior wall extending from outer peripheral parts of the anterior sealing wall to extend over said end portion and, in use, being resiliently extended, on inflation of the inflatable cuff, to sealingly engage the posterior pharyngeal wall of the patient;
wherein the inflatable cuff is molded as single integral molding.

17. An artificial airway as claimed in claim 16, wherein the airway tube is molded with proximal and distal portions which are joined together, the distal portion including said end portion of the airway tube.

18. An artificial airway as claimed in claim 17, wherein the inflatable cuff is formed with a proximal spigot which overlies a region where the proximal and distal end portions are joined together.

\* \* \* \* \*